US011906529B1

(12) United States Patent
Santanam et al.

(10) Patent No.: US 11,906,529 B1
(45) Date of Patent: Feb. 20, 2024

(54) METHODS FOR TREATMENT AND DIAGNOSIS OF ENDOMETRIOSIS

(71) Applicant: Marshall University Research Corporation, Huntington, WV (US)

(72) Inventors: Nalini Santanam, Huntington, WV (US); Kristeena Ray Wright, Huntington, WV (US); Sarah Brunty, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 0 days.

(21) Appl. No.: 16/397,825

(22) Filed: Apr. 29, 2019

Related U.S. Application Data

(60) Provisional application No. 62/663,572, filed on Apr. 27, 2018.

(51) Int. Cl.
| | |
|---|---|
| *C12Q 1/6883* | (2018.01) |
| *G01N 33/68* | (2006.01) |
| *A61K 31/496* | (2006.01) |
| *A61K 31/5377* | (2006.01) |

(52) U.S. Cl.
CPC ....... *G01N 33/6893* (2013.01); *A61K 31/496* (2013.01); *A61K 31/5377* (2013.01); *C12Q 1/6883* (2013.01); *C12Q 2600/106* (2013.01); *C12Q 2600/178* (2013.01); *G01N 2333/4703* (2013.01); *G01N 2800/364* (2013.01)

(58) Field of Classification Search
None
See application file for complete search history.

(56) References Cited

U.S. PATENT DOCUMENTS

2009/0208939 A1\* 8/2009 Flores .................. C12Q 1/6883
435/6.12

OTHER PUBLICATIONS

Leeder (Epilepsia 1998 vol. 39 Suppl 7:S8-16) (Year: 1998).\*
Colon-Caraballo, M., Monteiro, J. B., & Flores, I. (2015). H3K27me3 is an Epigenetic Mark of Relevance in Endometriosis. Reprod Sci, 22(9), 1134-1142. doi: 10.1177/1933719115578924.
Colon-Caraballo, M., Torres-Reveron, A., Soto-Vargas, J.L., Young, S.L., Lessey, B., Mendoza, A., Urrutia, R.,& Flores, I. (2018). Effects of histone methyltransferase inhibition in endometriosis. Biology of Reproduction, 99(2), 293-307. doi: 10.1093/biolre/ioy030.
Escobar, T. M., Kanellopoulou, C., Kugler, D. G., Kilaru, G., Nguyen, C. K., Nagarajan, V., Muljo, S. A. (2014). miR-155 activates cytokine gene expression in Th17 cells by regulating the DNA-binding protein Jarid2 to relieve polycomb-mediated repression. Immunity, 40(6), 865-879. doi: 10.1016/j.immuni.2014.03.014.
Ghislin, S., Deshayes, F., Middendorp, S., Boggetto, N., & Alcaide-Loridan, C. (2012). PHF19 and Akt control the switch between proliferative and invasive states in melanoma. Cell Cycle, 11(8), 1634-1645. doi: 10.4161/cc.20095.
Guo, S. W. (2009). Epigenetics of endometriosis. Mol Hum Reprod, 15(10), 587-607. doi: 10.1093/molehr/gap064.
Jablonski, K. A., Gaudet, A. D., Amici, S. A., Popovich, P. G., & Guerau-De-Arellano, M. (2016). Control of the Inflammatory Macrophage Transcriptional Signature by miR-155. PLoS One, 11(7), e0159724. doi: 10.1371/journal.pone.0159724.
Kohlhaas, S., Garden, O. A., Scudamore, C., Turner, M., Okkenhaug, K., & Vigorito, E. (2009). Cutting edge: the Foxp3 target miR-155 contributes to the development of regulatory T cells. J Immunol, 182(5), 2578-2582. doi: 10.4049/jimmunol.0803162.
Landeira, D., & Fisher, A. G. (2011). Inactive yet indispensable: the tale of Jarid2. Trends Cell Biol, 21(2), 74-80. doi: 10.1016/j.tcb.2010.10.004.
Li, G., Margueron, R., Ku, M., Chambon, P., Bernstein, B. E., & Reinberg, D. (2010). Jarid2 and PRC2, partners in regulating gene expression. Genes Dev, 24(4), 368-380. doi: 10.1101/gad.1886410.
Palma, C. A., Al Sheikha, D., Lim, T. K., Bryant, A., Vu, T. T., Jayaswal, V., & Ma, D. D. (2014). MicroRNA-155 as an inducer of apoptosis and cell differentiation in Acute Myeloid Leukaemia. Mol Cancer, 13, 79. doi: 10.1186/1476-4598-13-79.
Pasini, D., Cloos, P. A., Walfridsson, J., Olsson, L., Bukowski, J. P., Johansen, J. V., Helin, K. (2010). JARID2 regulates binding of the Polycomb repressive complex 2 to target genes in ES cells. Nature, 464(7286), 306-310. doi: 10.1038/nature08788.
Qin, S., Guo, Y., Xu, C., Bian, C., Fu, M., Gong, S., & Min, J. (2013). Tudor domains of the PRC2 components PHF1 and PHF19 selectively bind to histone H3K36me3. Biochem Biophys Res Commun, 430(2), 547-553. doi: 10.1016/j.bbrc.2012.11.116.
Ray, K., Fahrmann, J., Mitchell, B., Paul, D., King, H., Crain, C., Santanam, N. (2015). Oxidation-sensitive nociception involved in endometriosis-associated pain. Pain, 156(3), 528-539. doi: 10.1097/01.j.pain.0000460321.72396.88.
Ray, K. L., Mitchell, B. L., & Santanam, N. (2014). Power over pain: a brief review of current and novel interventions for endometriosis-associated pain. Journal of Endometriosis and Pelvic Pain Disorders, 6(4), 163-173. doi: 10.5301/je.5000199.
Rong, R., Ramachandran, S., Santanam, N., Murphy, A. A., & Parthasarathy, S. (2002). Induction of monocyte chemotactic protein-1 in peritoneal mesothelial and endometrial cells by oxidized low-density lipoprotein and peritoneal fluid from women with endometriosis. Fertil Steril, 78(4), 843-848.

(Continued)

*Primary Examiner* — Katherine D Salmon
(74) *Attorney, Agent, or Firm* — Stites & Harbison, PLLC; Terry L. Wright

(57) ABSTRACT

Methods and assays for diagnosis or prognosis of endometriosis include comparing an expression level or activity of miR-155 and JARID2 in a sample to detect a measurable difference. Therapeutic methods for treating endometriosis in a subject comprise identifying a subject as having a decreased expression level and/or activity of JARID2 in a sample obtained from the subject; and administering an agent that inhibits an activity of an miRNA that targets JARID2 or an agent that inhibits EZH2. Methods for screening for a compound useful for treating endometriosis are also provided and include contacting a cell with an effective amount of a test compound, and detecting whether the expression level or activity level of JARID2 or miR-155 in the cell is altered in the presence of the test compound.

7 Claims, 23 Drawing Sheets

(56) References Cited

OTHER PUBLICATIONS

Santanam, N., Kavtaradze, N., Murphy, A., Dominguez, C., & Parthasarathy, S. (2013). Antioxidant supplementation reduces endometriosis-related pelvic pain in humans. Transl Res, 161(3), 189-195. doi: 10.1016/j.trsl.2012.05.001.

Shen, Z., Chen, L., Yang, X., Zhao, Y., Pier, E., Zhang, X., Xiong, Y. (2013). Downregulation of Ezh2 methyltransferase by FOXP3: new insight of FOXP3 into chromatin remodeling? Biochim Biophys Acta, 1833(10), 2190-2200. doi: 10.1016/j.bbamcr.2013.05.014.

Son, J., Shen, S. S., Margueron, R., & Reinberg, D. (2013). Nucleosome-binding activities within JARID2 and EZH1 regulate the function of PRC2 on chromatin. Genes Dev, 27(24), 2663-2677. doi: 10.1101/gad.225888.113.

Wright, K., Mitchell, B., Santanam, N. (2017). Redox regulation of microRNAs in endometriosis-associated pain. Redox Biology, 12, 956-966. doi: https://doi.org/10.1016/j.redox.2017.04.037.

Xiong, Y., Khanna, S., Grzenda, A. L., Sarmento, O. F., Svingen, P. A., Lomberk, G. A., Faubion, W. A., Jr. (2012). Polycomb antagonizes p300/CREB-binding protein-associated factor to silence FOXP3 in a Kruppel-like factor-dependent manner. J Biol Chem, 287(41), 34372-34385. doi: 10.1074/jbc.M111.325332.

Yao, Y., Li, G., Wu, J., Zhang, X., & Wang, J. (2015). Inflammatory response of macrophages cultured with Helicobacter pylori strains was regulated by miR-155. Int J Clin Exp Pathol, 8(5), 4545-4554.

Momeni-Moghaddam, M. (2019). EZH2 Gene Silencing Cann Affect the Expression of miR-155 and TP53INPI. Journal of Cell and Molecular Research, 11 (1), pp. 37-41.

Brown, C., et al. (2018). FoxP3 and miR-155 cooperate to control the invasive potential of human breast cancer cells by down regulating ZEB2 independently of ZEB1. Oncotarget, vol. 9, No. 45, pp. 27708-27727.

Yun, J., et al. (2019). miR-155 harnesses Phf19 to potentiate cancer immunotherapy through epigenetic reprogramming of CD8+ T cell fate. Nature Communications 10:2157.

* cited by examiner

| miRNA | Fold Up/Down Regulation (Test/Control) |
|---|---|
| hsa-miR-30c | 4.308 |
| hsa-miR-30b | 3.908 |
| hsa-miR-10a | 2.697 |
| hsa-miR-29a | 6.460 |
| hsa-miR-26a | 4.760 |
| hsa-miR-148a | 4.409 |
| hsa-miR-181a | 2.234 |
| hsa-miR-30e | 2.896 |

METHODS FOR TREATMENT AND DIAGNOSIS OF ENDOMETRIOSIS

RELATED APPLICATIONS

This application claims priority from U.S. Provisional Application Ser. No. 62/663,572, filed Apr. 27, 2018, the entire disclosure of which is incorporated herein by this reference.

TECHNICAL FIELD

The presently-disclosed subject matter relates to methods for treatment and/or diagnosis of endometriosis. In particular, certain embodiments of the presently-disclosed subject matter relate to methods for treatment and/or diagnosis of endometriosis based on an expression level or activity of JARID2, a regulator of the PRC2 complex, in a biological sample obtained from a subject.

INTRODUCTION

Endometriosis is generally defined by the presence of endometrial tissue in ectopic locations, typically in or around the peritoneal cavity. While the exact prevalence of endometriosis is likely underrepresented, most sources cite a minimum of 10% of women in their reproductive years have this disease. Primarily described as a hormonal disorder, the pathogenesis of endometriosis has also been linked to immunological/inflammatory, genetic, and environmental factors, with chronic pelvic pain associated with endometriosis attributed to hormonal and immune aberrations that alter the makeup of peritoneal fluid (PF) and impact surrounding tissues. Though therapeutic agents such as non-steroidal anti-inflammatory drugs (NSAIDs) and gonadotropin releasing hormone (GnRH) inhibitors are currently useful for treatment of pain associated with endometriosis, none of those therapeutic agents have proven to be effective long term. To date, that long term inability to treat endometriosis has been attributed to the reoccurrence of the disease in afflicted subjects.

More recently, the role of epigenetics in the development and progression of the disorder has been investigated. Epigenetic mechanisms are heritable changes to one's phenotype that are not associated with a change in nucleotide sequence and include DNA methylation, post-translational modifications to histone proteins, and often microRNAs. It has been determined that the trimethylation of histone 3 lysine 27 (H3K27me3) plays a role in endometriosis. This histone modification has only one known methyltransferase, EZH2, the catalytic subunit of the epigenetic complex PRC2.

Polycomb repressive complex 1 (PRC1), polycomb repressive complex 2 (PRC2), and PhoRC all form the PcG complexes, with the former two typically being the subject of extensive epigenetic research. The Polycomb Repressive Complex 2 (PRC2) consists of four core proteins, RbAp46/48, Embryonic Ectoderm Development (EED), Suppressor of Zeste 12 (SUZ12), and Enhancer of Zeste Homolog 2 (EZH2), the catalytic subunit of the PRC2 complex. These components work together to regulate chromatin structure via tri-methylation of lysine 27 on histone 3 (H3K27me3), which is also known to interact with PRC1. EED binds the histone site while EZH2 methylates it, with the help of SUZ12. This modification leads to the formation of closed chromatin structure (heterochromatin) and thus marks transcriptional repression, as further demonstrated by the presence of other co-factors. Little is known about the mechanistic role of this complex in the pathophysiology of endometriosis. One recent study in endometriosis showed heightened expression of EZH2 and trimethylation of H3K27 in secretory endometrium and endometriotic lesions. Additionally, an endometriosis cell culture study has shown that inhibition of PGE2 receptors EP3 and EP4 are coincident with decreased EZH2 expression, supporting a role for PRC2 in endometriosis-associated pain.

It is also appreciated that the PRC2 complex (specifically EZH2) is, at least partly, regulated by Jumonji AT-Rich Interactive Domain Containing 2 (JARID2 or sometimes referred to herein as Jumonji protein 2), a member of the jumonji family of histone demethylases. The jumonji family is the largest family of histone demethylases, and all but JARID2 contain the catalytic JmjC domain responsible for histone demethylation. Due to its cross-talk with EZH2 and PRC2 activity in embryonic stem cells, JARID2 is thought to play a role in the development and potentially in the progression of cancer. In a study of acute lymphoid leukemia, researchers determined that miR-155-5p induced cell death via a network of mechanisms, including regulation of cyclinD1 by JARID2. Others believe that miR-155-5p could have evolved to regulate PRC2 by tweaking JARID2 expression. Interestingly, miR-155-5p is an established promoter of inflammation via regulation of macrophages and cytokines.

miR-155 is highly expressed in regulatory T-cells (Tregs), where it is targeted by the transcription factor FOXP3, a known tumor suppressor. Though limited in evidence, FOXP3 plays a role in the inflammatory aspect of endometriosis. The prevalence of FOXP3+ Tregs in an endometriotic environment during secretory phase prevented leukocyte recruitment to the sites of endometriosis. Additionally, PF from women with endometriosis has a higher concentration of FOXP3-expressing TCD4+CD25$^{hi}_{gh}$ cells than the PF of control patients.

Over the past several years, there has been a lack of consistent findings regarding FOXP3 expression in endometriotic lesions and eutopic tissues of endometriosis patients. Most recently, high FOXP3 expression was observed in deep rectosigmoid lesions but lower expression in the eutopic endometrium of endometriosis patients with chronic pelvic pain. These studies provide further evidence that the immunological aspects of endometriosis are at least partly responsible for endometriosis-associated pain.

FOXP3 also has an indirect relationship with the EZH2 component of PRC2. In breast cancer models, overexpression of FOXP3 protein not only lessened the proliferative effects of EZH2, but also enhanced degradation of EZH2 protein. Conversely, there is evidence that trimethylation of H3K27 by EZH2 is capable of silencing FOXP3 promoter regions, therefore leading to aberrant Treg cell differentiation and function. These studies suggest a complex interplay between epigenetic mediators, PRC2 complex, miR-155-5p and the inflammatory mediator FOXP3.

Accordingly, identification of alternative targets that play a role in endometriosis and nociception would be highly beneficial in the treatment and diagnosis of endometriosis.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes methods for the treatment or diagnosis of endometriosis based on an expression level or activity of JARID2 and/or other biomarkers present in a biological sample obtained from a subject. In some embodiments of the presently-disclosed subject matter, a method for diagnosis or prognosis of endometriosis in a subject is provided that comprises the steps of: providing a biological sample from the subject; determining an expression level or activity in the sample of at least one biomarker selected from miR-155 and JARID2; and then comparing the expression level or activity of the at least one biomarker in the sample, if present, to a control expression level or activity of the at least one biomarker. In some embodiments, the subject can then be diagnosed as having endometriosis or a risk thereof if there is a measurable difference in the expression level or activity of the at least one biomarker in the sample as compared to the control level. In some embodiments, the endometriosis is eutopic endometriosis or ectopic endometriosis. In some embodiments, the subject is human, has endometriosis, and/or has pain associated with the endometriosis.

With respect to the biological sample, in some embodiments, the biological sample comprises peritoneal fluid, blood, plasma, serum, or endometrial tissue. In some embodiments, determining the expression level or activity in the biological sample of the at least one biomarker comprises determining the expression level or activity in the sample of the at least one biomarker using mass spectrometry (MS) analysis, immunoassay analysis, or both.

In some embodiments of the diagnostic methods, upon determining an expression level or activity of at least one of the biomarkers, such as, in certain embodiments, JARID2, a treatment for the endometriosis is subsequently selected or modified based on the determined expression level or activity of the at least one biomarker. In some embodiments, a method for determining whether to initiate or continue prophylaxis or treatment of an endometriosis in a subject is provided that comprises the steps of: providing a series of biological samples over a time period from the subject; analyzing the series of biological samples to determine an expression level or activity in each of the biological samples of at least one biomarker selected from miR-155 and JARID2; and comparing any measurable change in the expression level or activity of the at least one biomarker in each of the biological samples to thereby determine whether to initiate or continue the prophylaxis or therapy of the endometriosis. In some embodiments, based on the expression level or activity of JARID2 in the sample, a determination as to whether to initiate or continue prophylaxis or therapy of the endometriosis is made.

Further provided, in some embodiments of the presently-disclosed subject matter, are methods for treatment of endometriosis in a subject. In some embodiments, a method for treating endometriosis in a subject is provided that comprises the steps of identifying a subject as having a decreased expression level and/or activity of JARID2 in a biological sample obtained from the subject; and then administering an effective amount of a therapeutic agent that inhibits an activity of an miRNA that targets JARID2 or an agent that inhibits EZH2. In some embodiments, the miRNA is miR-155. In some embodiments, the therapeutic agent that inhibits EZH2 is selected from GSK 126 and EPZ-6438.

Still further provided, in some embodiments of the presently-disclosed subject matter, are assays for assessing endometriosis in a subject. In some embodiments, an assay for assessing endometriosis is provided that comprises: applying an agent capable of affecting detection of an expression level or activity of JARID2 or miR-155 in a biological sample obtained from a subject; and determining the expression level or activity of JARID2 or miR-155 in the biological sample. In some embodiments, the activity level of JARID2 is determined by determining an amount and/or activity of EZH2 and/or H3k27me3 in the biological sample.

Even further provided, in some embodiments, are methods for screening for a compound useful for treating endometriosis. In some embodiments, a method for screening for a compound useful for treating endometriosis, includes: contacting a cell with an effective amount of a test compound; and detecting an expression level or activity level of JARID2 or miR-155 in the cell in the presence of the test compound.

Further features and advantages of the present invention will become evident to those of ordinary skill in the art after a study of the description, figures, and non-limiting examples in this document.

BRIEF DESCRIPTION OF THE DRAWINGS

FIG. 9A shows Western blots of EZH2, H3K27me3, and FOXP3 in control (EuNN), eutopic endometriosis (EuYY), and ectopic endometriosis (EcYY) tissues (n=6). Each blot represents identical sample loading, antibody dilutions, and overall protocol. FIG. 9B is a graph showing densitometry analysis of Western blots, showing protein expression relative to β-actin; p>0.05. FIG. 9C is a graph and table showing relative mRNA expression of polycomb repressor complex 2 (PRC2) elements in EuNN (n=3), EuYY (n=7) and EcYY tissues (n=4). In general, these elements were underexpressed in eutopic endometriosis tissues compared to control tissues. There was general overexpression in ectopic endometriosis tissues, especially in EZH2 (p=0.06)

DESCRIPTION OF EXEMPLARY EMBODIMENTS

Figures 1, 2A:
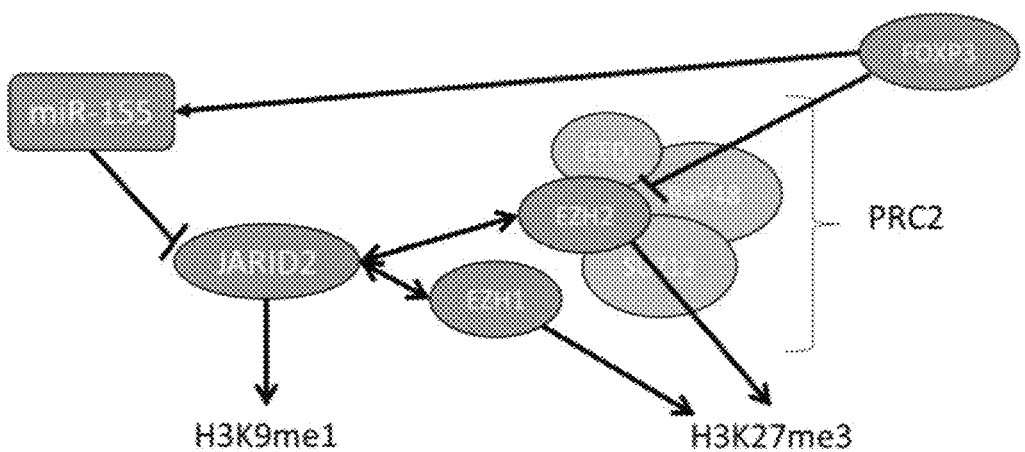
FIG. 1 is a schematic diagram showing an epigenetic mechanism contributing to pain and progression of endometriosis in accordance with the presently-disclosed subject matter. Arrows indicate activation or general targeting while "T" bars indicate inhibition.
FIG. 2A includes a table showing the fold up/down regulation of miRNAs differentially expressed in tissues from endometriosis patients relative to control patients, and that are known to target the 3'UTR of JARID2.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended), "consist of" (closed ended), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is based, at least in part, on the discovery that that epigenetics plays a role in endometriotic pain. In this regard, during the course and development of the present application epigenetic markers from endometriosis patients were examined and it was surprisingly discovered that the PRC2 complex, which regulates histone modification and in turn affects gene function, was differently expressed in subjects exhibiting symptoms of endometriosis. Moreover, it was further surprisingly found that micro-RNA (miR)-155 and JARID2 (jumonji, AT rich interactive domain 2) complex was an important regulator of the PRC2 complex. Accordingly, in some embodiments of the present invention, miR-155, JARID2, and combinations and complexes thereof provide targets for the diagnosis and treatment of endometriosis.

In some embodiments of the presently-disclosed subject matter, methods and systems for diagnosis and prognosis of endometriosis are thus provided that make use of at least one biomarker. In some embodiments, the at least one biomarker used to diagnose endometriosis can be JARID2 or miR-155 (JARID2 GENBANK No.: NM_004973.4; miR-155 GENBANK No.: NR_030784).

The exemplary human biomarkers described herein are not intended to limit the present subject matter to human polypeptide biomarkers or mRNA biomarkers only. Rather, the present subject matter encompasses biomarkers across animal species that are associated with endometriosis.

A "biomarker" is a molecule useful as an indicator of a biologic state in a subject. With reference to the present subject matter, the biomarkers disclosed herein can be polypeptides that exhibit a change in expression level or activity, which can be correlated with the risk of developing, the presence of, or the progression of endometriosis in a subject. In addition, the biomarkers disclosed herein are inclusive of messenger RNAs (mRNAs) encoding the biomarker polypeptides, as measurement of a change in expression of an mRNA can be correlated with changes in expression of the polypeptide encoded by the mRNA. As such, determining an amount of a biomarker in a biological sample is inclusive of determining an amount of a polypeptide biomarker and/or an amount of an mRNA encoding the polypeptide biomarker either by direct or indirect (e.g., by measure of a complementary DNA (cDNA) synthesized from the mRNA) measure of the mRNA.

In some embodiments of the presently-disclosed subject matter, a method for diagnosing endometriosis in a subject is provided that includes the steps of: providing a biological sample from the subject; determining an expression level or activity in the sample of at least one biomarker selected from miR-155, JARID2, and/or combinations thereof; and comparing the expression level or activity of the at least one biomarker in the sample, if present, to a control expression level or activity of the at least one biomarker. In some embodiments, the subject is then diagnosed as having endometriosis or a risk thereof if there is a measurable difference in the expression level or activity of the at least one biomarker in the sample as compared to the control level. In some embodiments, the endometriosis that is diagnosed in eutopic endometriosis or ectopic endometriosis. In some embodiments, the activity level of JARID2 is determined by determining an amount and/or activity of EZH2 and/or H3k27me3 in the biological sample.

The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a marker, the amount (including presence or absence) of which is indicative of the presence, severity, or absence of the condition.

Along with diagnosis, clinical disease prognosis is also an area of great concern and interest. It is important to know the stage and rapidity of advancement of the endometriosis in order to plan the most effective therapy. If a more accurate prognosis can be made, appropriate therapy, and in some instances less severe therapy for the patient can be chosen. Measurement of biomarker levels disclosed herein can be useful in order to categorize subjects according to advancement of endometriosis who will benefit from particular therapies and differentiate from other subjects where alternative or additional therapies can be more appropriate.

As such, "making a diagnosis" or "diagnosing", as used herein, is further inclusive of determining a prognosis, which can provide for predicting a clinical outcome (with or without medical treatment), selecting an appropriate treatment (or whether treatment would be effective), or monitoring a current treatment and potentially changing the treatment, based on the measure of diagnostic biomarker levels disclosed herein.

The phrase "determining a prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of test biomarkers. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not expressing the biomarker or expressing it at a reduced level), the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a biomarker level (e.g., quantity of expression in a sample) of greater than a control level in some embodiments can signal that a subject is more likely to suffer from or experience endometriosis than subjects with a level less than or equal to the control level, as determined by a level of statistical significance. Additionally, a change in marker concentration from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments, a threshold degree of change in the level of a prognostic or diagnostic biomarker can be established, and the degree of change in the level of the indicator in a biological sample can simply be compared to the threshold degree of change in the level. A preferred threshold change in the level for markers of the presently disclosed subject matter is about 5%, about 10%, about 15%, about 20%, about 25%, about 30%, about 50%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments of the presently-disclosed subject matter, multiple determination of one or more diagnostic or prognostic biomarkers can be made, and a temporal change in the biomarker can be used to monitor the progression of disease and/or efficacy of appropriate therapies directed against the disease. In such an embodiment for example, one might expect to see a decrease or an increase in the biomarker(s) over time during the course of effective therapy. Thus, the presently disclosed subject matter provides in some embodiments a method for determining treatment efficacy and/or progression of endometriosis in a subject. In some embodiments, the method comprises determining an amount of at least one biomarker associated with endometriosis, such as for example at least one biomarker selected from miR-155 and JARID2, in biological samples collected from the subject at a plurality of different time points and comparing the amounts of the at least one biomarker in the samples collected at different time points. For example, a first time point can be selected prior to initiation of a treatment and a second time point can be selected at some time after initiation of the treatment. One or more biomarker levels can be measured in each of the samples taken from different time points and qualitative and/or quantitative differences noted. A change in the amounts of the biomarker levels from the first and second samples can be correlated with determining treatment efficacy and/or progression of the disease in the subject.

The terms "correlated" and "correlating," as used herein in reference to the use of diagnostic and prognostic biomarkers, refers to comparing the presence or quantity of the biomarker in a subject to its presence or quantity in subjects known to suffer from, or known to be at risk of, a given condition (e.g., endometriosis); or in subjects known to be free of a given condition, i.e. "normal individuals." For example, a biomarker level in a biological sample can be compared to a level known to be associated with a specific type of endometriosis. The sample's biomarker level is said to have been correlated with a diagnosis; that is, the skilled artisan can use the biomarker level to determine whether the subject suffers from or is experiencing a specific type of endometriosis, and respond accordingly. Alternatively, the sample's biomarker level can be compared to a control marker level known to be associated with a good outcome (e.g., the absence of endometriosis), such as an average level found in a population of normal subjects.

In certain embodiments, a diagnostic or prognostic biomarker is correlated to a condition or disease by merely its presence or absence. In other embodiments, a threshold level of a diagnostic or prognostic biomarker can be established, and the level of the indicator in a subject sample can simply be compared to the threshold level.

As noted, in some embodiments, multiple determination of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type of endometriosis, or a given prognosis. Likewise, a decrease in the marker from the initial time to the second time can be indicative of a particular type of endometriosis, or a given prognosis. Furthermore, in some embodiments, the degree of change of one or more markers can be related to the severity of endometriosis and future adverse events.

The skilled artisan will understand that, while in certain embodiments comparative measurements can be made of the same diagnostic marker at multiple time points, one can also measure a given marker at one time point, and a second marker at a second time point, and a comparison of these markers can provide diagnostic information.

With regard to the step of providing a biological sample from the subject, the term "biological sample" as used herein refers to any body fluid or tissue potentially comprising metabolites. In some embodiments, for example, the biological sample can be a blood sample, a serum sample, a plasma sample, or sub-fractions thereof. In some embodiments, the biological sample comprises peritoneal fluid or endometrial tissue.

Turning now to the step of identifying an expression level or activity of one or more markers in the biological sample, various methods known to those skilled in the art can be used to identify the one or more markers in the provided biological sample. In some embodiments, determining the amount of biomarkers in samples comprises using a RNA measuring assay to measure miRNA or mRNA encoding biomarker polypeptides in the sample and/or using a protein measuring assay to measure amounts of biomarker polypeptides in the sample.

In certain embodiments, the amounts of biomarkers can be determined by probing for an miRNA or for mRNA of the biomarker in the sample using any RNA identification assay known to those skilled in the art. Briefly, RNA can be extracted from the sample, amplified, converted to cDNA, labeled, and allowed to hybridize with probes of a known sequence, such as known RNA hybridization probes (selective for mRNAs encoding biomarker polypeptides) immobilized on a substrate, e.g., array, or microarray, or quantitated by real time PCR (e.g., quantitative real-time PCR, such as available from Bio-Rad Laboratories, Hercules, California, U.S.A.). Because the probes to which the nucleic acid molecules of the sample are bound are known, the molecules in the sample can be identified. In this regard, DNA probes for one or more biomarkers (e.g., miR-155 or JARID2) can be immobilized on a substrate and provided for use in practicing a method in accordance with the present subject matter.

In some embodiments, determining the amount of biomarkers in samples comprises the use of mass spectrometry and/or immunoassay devices and methods to measure polypeptides in samples, although other methods are well known to those skilled in the art as well. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Thus, in certain embodiments of the presently-disclosed subject matter, the marker peptides are analyzed using an immunoassay. The presence or amount of a marker (e.g., JARID2) can be determined using antibodies or fragments thereof specific for each marker and detecting specific binding. For example, in some embodiments, the antibody specifically binds JARID2, which is inclusive of antibodies that bind the full-length peptide or a fragment thereof. In some embodiments, the antibody is a monoclonal antibody, such as an anti-JARID2 monoclonal antibody. In other embodiments, the antibody is a polyclonal antibody.

Any suitable immunoassay can be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies or fragments thereof specific for the markers is also contemplated by the presently-disclosed subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

In some embodiments, mass spectrometry (MS) analysis can be used alone or in combination with other methods (e.g., immunoassays) to determine the presence and/or quantity of the one or more biomarkers of interest in a biological sample. In some embodiments, the MS analysis comprises matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers, such as for example triple quadrupole mass spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated herein by this reference.

With further respect to the measurement of the biomarkers described herein, in some embodiments, the miR-155 or JARID2 biomarker is detected in the sample using a method selected from the group consisting of ELISA, Luminex, FACs, Western blot, dot blot, immunoprecipitation, immunohistochemistry, immunocytochemistry, immunofluorescence, immunodetection methods, optical spectroscopy, radioimmunoassay, mass spectrometry, HPLC, qPCR, RTqPCR, multiplex qPCR, SAGE, RNA-seq, microarray analysis, FISH, MassARRAY technique, and combinations thereof.

Although certain embodiments of the methods only call for a qualitative assessment of the presence or absence of the one or more markers in the biological sample, other embodiments of the method call for a quantitative assessment of the amount of each of the one or more markers in the biological sample. Such quantitative assessments can be made, for example, using one of the above mentioned methods, as will be understood by those skilled in the art.

In certain embodiments of the method, a subject is identified having endometriosis upon identifying the one or more biomarkers in a biological sample obtained from the subject. In other embodiments of the method, the identification of one or more of such markers in a biological sample obtained from the subject results in the subject being identified as having a risk of endometriosis.

In certain embodiments of the method, it can be desirable to include a control sample that is analyzed concurrently with the biological sample, such that the results obtained from the biological sample can be compared to the results obtained from the control sample. Additionally, it is contemplated that standard curves can be provided, with which assay results for the biological sample can be compared. Such standard curves present levels of biomarkers as a function of assay units, i.e., fluorescent signal intensity, if a fluorescent signal is used. Using samples taken from multiple donors, standard curves can be provided for control levels of the one or more markers in normal tissue.

The analysis of markers can be carried out separately or simultaneously with additional markers within one test sample. For example, several markers can be combined into one test for efficient processing of a multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker levels over time. Increases or decreases in marker levels, as well as the absence of change in marker levels, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of markers can be carried out in a variety of physical formats as well. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

As mentioned above, depending on the embodiment of the method, identification of the one or more markers can be a qualitative determination of the presence or absence of the markers, or it can be a quantitative determination of the concentration of the markers. In this regard, in some embodiments, the step of identifying the subject as having endometriosis or a risk thereof requires that certain threshold measurements are made, i.e., the levels of the one or more markers in the biological sample exceed control level. In certain embodiments of the method, the control level is any detectable level of the marker. In other embodiments of the method where a control sample is tested concurrently with the biological sample, the control level is the level of detection in the control sample. In other embodiments of the method, the control level is based upon and/or identified by a standard curve. In other embodiments of the method, the control level is a specifically identified concentration, or concentration range. As such, the control level can be chosen, within acceptable limits that will be apparent to those skilled in the art, based in part on the embodiment of the method being practiced and the desired specificity, etc.

In some embodiments of the presently-disclosed subject matter, a system, kit, or assay for diagnosing endometriosis in a subject is provided, or a system, kit, or assay for determining whether to initiate or continue prophylaxis or treatment of endometriosis in a subject is provided. Such systems, kits, or assays can be provided, for example, as commercial kits that can be used to test a biological sample, or series of biological samples, from a subject. The system can also include certain samples for use as controls. The system can further include one or more standard curves providing levels of markers as a function of assay units.

In some embodiments, a system for the analysis of biomarkers is provided that comprises antibodies having specificity for one or more markers associated with endometriosis. Such a system can comprise devices and reagents for the analysis of at least one test sample. The system can further comprise instructions for using the system and conducting the analysis. Optionally the systems can contain one or more reagents or devices for converting a marker level to a diagnosis or prognosis of the subject.

Still further provided, in some embodiments of the presently-disclosed subject matter, are methods for treating endometriosis in a subject. In some embodiments, a method of treating endometriosis is provided that comprises administering to a subject an effective amount of a therapeutic agent that increases an expression level and/or an activity of JARID2. In some embodiments, a therapeutic method is provided that comprises the steps of: identifying a subject as having a decreased expression level and/or activity of JARID2 in a biological sample obtained from the subject; and administering an effective amount of a therapeutic agent that inhibits an activity of an miRNA that targets JARID2 or an agent that inhibits EZH2. In some embodiments, the therapeutic agent comprises an agent that inhibits an activity of an miRNA that targets JARID2. In some embodiments, the miRNA is miR-155. In some embodiments, the therapeutic agent comprises an agent that inhibits EZH2. In some embodiments, the EZH2 inhibitor is GSK 126 or EPZ-6438.

The terms "treatment" or "treating" refer to the medical management of a subject with the intent to cure, ameliorate, stabilize, or reduce the presence of a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes: palliative treatment, or treatment designed for the relief of symptoms rather than the curing of the disease, pathological condition, or disorder; preemptive treatment, or treatment directed to minimizing or partially or completely inhibiting the development of the associated disease, pathological condition, or disorder; and supportive treatment, or treatment employed to supplement another therapy directed toward the improvement of the associated disease, pathological condition, or disorder.

For administration of a therapeutic agent as disclosed herein, conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate kg factor. In an adult human, 100 mg/kg is equivalent to 100 mg/kg×37 kg/sq m=3700 mg/m².

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered intravenously to treat a disease or disorder.

Regardless of the route of administration, the therapeutic agents used in accordance with the presently-disclosed subject matter are typically administered in an amount effective to achieve the desired response. As such, the term "effective amount" is used herein to refer to an amount of the therapeutic composition sufficient to produce a measurable biological response. Actual dosage levels of active ingredients in a therapeutic composition used in accordance with the presently-disclosed subject matter can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Florida; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pennsylvania; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) *Toxicol. Lett.* 100-101:255-263.

With respect to the presently-disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

Even further provided, in some embodiments of the presently-disclosed subject matter, are methods for screening for a compound useful for treating endometriosis. In some embodiments, a method for screening for a compound useful for treating endometriosis is provided that comprises: contacting a cell with an effective amount of a test compound; and detecting whether the expression level or activity level of JARID2 in the cell is increased in the presence of the test compound.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

EXAMPLES

Materials and Methods for Examples 1-7

Human Subject Participants: Women ages 21 to 60 years, undergoing tubal ligation or having non-endometriosis disorders (controls) or patients with endometriosis (laparoscopically diagnosed followed by pathological confirmation and/or patients with symptoms) were recruited from the Obstetrics-Gynecology clinic at Cabell Huntington Hospital, Joan C. Edwards School of Medicine, Marshall University, in Huntington, WV. In the study, endometriosis patients were diagnosed with stage I/II peritoneal endometriosis. The HIPAA-compliant study was approved by the Institutional Review Board of the Marshall University School of Medicine and was carried out per the principles of the Declaration of Helsinki. All patients were consented prior to the study. All women completed a gynecologic/infertility history form, a pre-operative quality of life questionnaire and assessment of pain using a visual analog scale for assessment of endometriosis associated pain (dysmenorrhea, non-menstrual pelvic pain, dyspareunia, and dyschesia) (adapted from the validated International Pelvic Pain Society's Pelvic Assessment Form). Date of their last menstrual period was used to assess their cycle time. The inclusion criteria included women ages 21-60 years old, with normal menstrual cycles and otherwise in normal health (except for pain and endometriosis) who have not been on any hormonal medication for at least one month before sample collection. Exclusion criteria included subjects with current medical illnesses such as diabetes, cardiovascular disease, hyperlipidemia, hypertension, systemic lupus erythematosus or rheumatologic disease, positive HIV/AIDS, active infection. Subjects were asked to stop multivitamins that contain high levels of antioxidants and anti-inflammatory medications one month prior to sample collection.

RNA/Protein Isolation in Peritoneal Fluid-treated Cells
Peritoneal fluid (PF) (devoid of blood contamination) was collected on ice from all women during laparoscopic surgery. Peritoneal fluid was spun at 2000×g to remove any cellular debris. The supernatant was used immediately for studies or stored in a −80° C. freezer for future use. To establish a cell model of the peritoneal environment, Ishikawa cells, a human (39-year-old woman) established endometrial cell line (Sigma-Aldrich, St. Louis, MO), were cultured in T75 flasks in complete media (DMEM/F12, 10% FBS, 1% Pen/Strep, 1% L-glutamine). These cells were used because they express characteristics similar to those of mature endometrial epithelial cells. Approximately 70% confluent cells were treated with 1% PF from patients for 48 hours in a DMEM/F12 media containing 1% charcoal-stripped FBS.

Patient peritoneal fluid (PF) groups were +endometriosis/+pain (YY-PF), +endometriosis/−pain (YN-PF), and −endometriosis/−pain (NN-PF, "control fluid"). The concentrations chosen were based on previously published studies. At the end of the 48-hour treatment, cells were collected using Qiazol Lysis reagent (Qiagen, Gaithersburg, MD) and RNA was isolated using the Qiagen miRNeasy Mini Kit. The quantity and quality of RNA were measured in the NanoDrop 2000 spectrophotometer. Cells were also collected in RIPA buffer with protease inhibitors (Thermo Scientific, USA) and protein concentrations were measured using a modified Lowry protocol.

Endometrial Tissue Collection and RNA/Protein Isolation: Endometrial (eutopic) tissues from control patients (EuNN), eutopic tissues from endometriosis (ovarian or peritoneal endometriosis, "endo") patients (EuYY), and ectopic endometriotic tissues (EcYY) from endo patients were removed during laparoscopy/laparotomy by a qualified physician. Biopsy fragments were immediately placed in RNAlater solution (Qiagen) and subsequently stored in a freezer at −80° C. RNA extraction from 100 mg of tissue (eutopic and ectopic) was carried out using Qiazol Lysis Reagent (Qiagen). Tissues were homogenized using zirconium oxide beads in a Bullet Blender® homogenizer (Next Advance, USA) and RNA was isolated using the Qiagen miRNeasy Mini Kit following the manufacturer's recommendations. The quantity and quality of RNA were measured in the NanoDrop 2000 spectrophotometer (Thermo Scientific, USA). Similarly, 50 mg of tissue was homogenized in RIPA buffer prior to protein estimation by a modified Lowry method.

mRNA expression in Tissues and PF-treated Ishikawa cells: RNA (which includes miRNA) isolated from the tissues and treated cells were used. cDNA synthesis from 1 µg of each sample was performed using iScript RT II Kit (Qiagen). mRNA expression was analyzed in the cDNA samples using SEER Green (Biorad, Hercules, CA) and the primers listed in Table 1. cDNA synthesis from 2 µg of each sample was performed using miScript RT Kit (Qiagen). To determine the expression of miR-29a, miR-148a, and miR-155 in tissues and PF-treated cells, the appropriate Qiagen Primer Assay Kit was used, following the manufacturer's protocol for qPCR. A primer assay for RNU6 was used for a qPCR housekeeping gene.

TABLE 1

Primer sequences for RT-qPCR analysis of epigenetic gene expression in patient tissues and PF-treated cells. Primers were designed using NCBI GenBank.

| GENE NAME | PRIMER TYPE | SEQUENCE |
| --- | --- | --- |
| EED | sense | 5'-CATTGGGCAATCAAGTTGGCA-3' |
|  | antisense | 5'-ACAAGTGTGGAGAAAAAGCCTG-3' |
| SUZ12 | sense | 5'-GTTACCGGTGAAGAAGCCGA-3' |
|  | antisense | 5'-TTGGCTTCTCAAAGGCCTGG-3' |
| EZH2 | sense | 5'-AAGGAGTTTGCTGCTGCTCT-3' |
|  | antisense | 5'-ATTAATGGTGGGGGTGCTGG-3' |
| JARID2 | sense | 5'-CTGCAGCACAAACGTGACTT-3' |
|  | antisense | 5'-CATCAGCGAAACGTGAAGGTC-3' |
| FOXP3 | sense | 5'-ACTGGGGTCTTCTCCCTCAA-3' |
|  | antisense | 5'-GGGATTTGGGAAGGTGCAGA-3' |

Protein expression in PF-treated cells and patient tissues: Total protein was measured using a modified Lowry method. Protein (35 µg) was separated on a 4-20% Tris-HCl gradient gel (Biorad) and transferred onto nitrocellulose membranes. After washing with Tris-buffered saline with Tween 20 (TBST), the membranes were blocked in 5% bovine serum albumin or 5% milk in TBST for 1 hour, then incubated at 4° C. overnight with anti-rabbit antibody against JARID2, FOXP3, EZH2, and H3K27me3 (1:1000, Cell Signaling, Danvers, MA) and anti-mouse against β-actin (1:4000, Sigma-Aldrich). Anti-rabbit antibody against H4 was diluted 1:20000. The membranes were washed and incubated with HRP-linked anti-rabbit or anti-mouse secondary antibody (1:6000, Sigma-Aldrich, St. Louis, MO) for one hour at room temperature. After washing, membranes were developed in HRP Substrate (Millipore, Temecula, CA) and imaged using the ChemiDoc system (Biorad). Densitometric levels of protein bands were quantified and expressed as their relative ratio to β-actin.

Cell Transfection with miR-155 mimic/antagonist: Cells were transfected using SiPORT™ NeoFX™ transfection agent (Ambion, Austin, TX) as recommended by the manufacturer. In short, the SiPORT™ NeoFX™ was diluted in Opti-MEM® Reduced Serum Media (Invitrogen, Carlsbad, CA) and incubated for 10 min at room temperature. miR-155 mimic (Pre-miR™), inhibitor (Anti-miR™), positive control (anti-let-7c), and negative control (Negative control #1) were diluted in Ishikawa media to a final concentration of 30 nM and then combined with the transfection agent and incubated for 10 min at room temperature. Transfection mixtures were added to 6-well plates and overlaid with cell suspensions. Cells were then incubated for 24 hours prior to treatment with peritoneal fluid from control and endometriosis patients, as previously described. Transfections were tested for effectiveness by collecting cells in Qiazol and using a miR-155 primer assay to assess miRNA expression. This transfection process was completed for collection of cells for protein and RNA and a miR-155-5p qPCR assay was used to verify transfection efficiency. RNA was isolated using the miRNeasy Mini Kit following the manufacturer's recommendations. Western blots and RT-qPCR were used (as previously described) to determine the expression of key downstream targets.

Chromatin Immunoprecipitation (ChIP): Approximately 70% confluent Ishikawa cells were treated with 1% PF from patients for 48 hours in a DMEM/F12 media containing 1% charcoal-stripped FBS. Proteins were cross-linked to proteins by adding formaldehyde (0.75% by volume) and allowing for a 10-minute incubation at room temperature. Glycine (0.5M) was added and incubated for an additional 10 minutes. Cells were twice rinsed with PBS, collected in 1 ml PBS, pelleted by centrifugation, and lysed in 300 μL of lysis buffer (1% SDS; 5 mM EDTA; 50 mM Tris-HCl, pH 8) plus protease inhibitors (Thermo Scientific). Cell extracts were sonicated on ice 3×10 seconds at 15% using Salisbury sonicator. Shearing was verified by running chromatin samples on an agarose gel and fragments averaged about 800 kD in size. After isolating 50 μl of each sample for INPUT, 100p per antibody were diluted 1:10 in dilution buffer (16.7 mM Tris-HCl, pH 8; 167 mM NaCl; 1.2 mM EDTA; 0.01% SDS; 1.1% Triton X-100) and rotated overnight at 4° C. with 2 μg of non-specific IgG (Santa Cruz) or ChIP-grade anti-JARID2 antibody (Cell Signaling, #13594). Antibody-chromatin complexes were collected using 5 μL of magnetic Dynabeads protein A beads (Invitrogen) with rotation at 4° C. for 90 min. Using magnetic separation (Life Technologies), beads were washed sequentially with low and high salt wash buffer, 0.25M LiCl wash buffer, and TE buffer. All samples (including INPUT) were incubated at 65° C. for 4 hours with elution buffer containing proteinase K. DNA concentration was determined by NanoDrop 2000 spectrophotometer and analyzed using the Human Polycomb & Trithorax Complexes EpiTect ChIP qPCR Array (Qiagen). This array consisted of primers for genes belonging to the polycomb and trithorax complexes (core, alternate, and additional components), as well as polycomb co-factors such as PHD finger protein 19 (PHF19) and heterochromatin (CBX) proteins. Percent enrichment and further statistical analysis was calculated using an SA Biosciences spreadsheet.

Statistical Analysis: Prism software (GraphPad, Inc., La Jolla, CA) was used for analysis of non-array qPCR data in human tissue and cell culture studies. All values were expressed as mean±standard error of the mean (SEM). A one-way ANOVA followed by Tukey's post-hoc test was used to detect differences in relative gene expression among treatment groups. Student's t-test was used to compare the means of mRNA and protein expression in various tissues and cell treatments. P values less than 0.05 were considered significant.

Figure 2B:
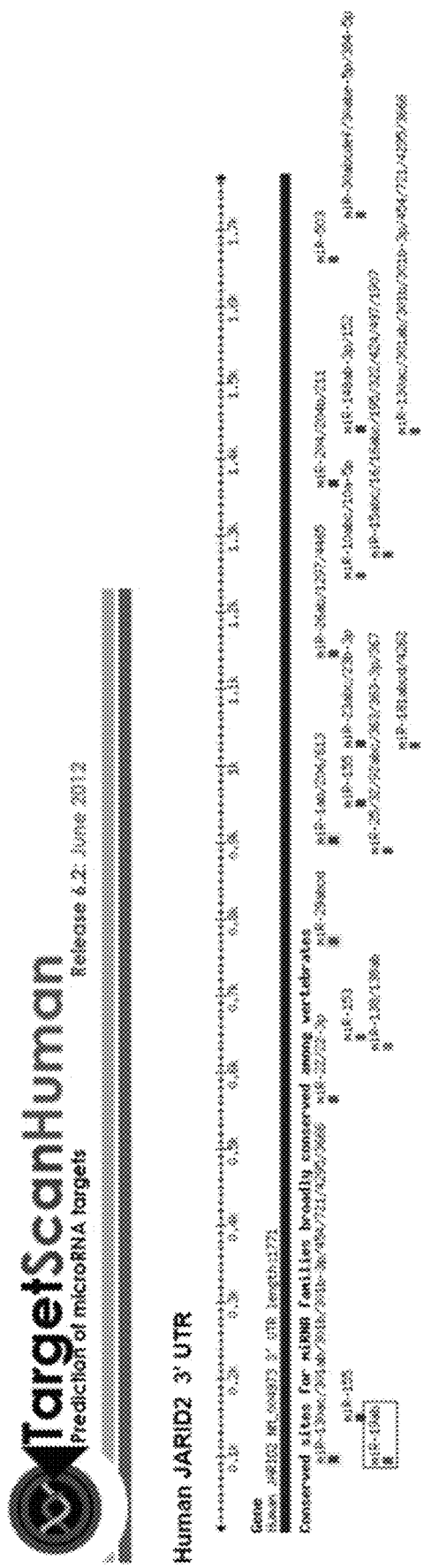
FIG. 2B shows a TargetScan analysis of 37 miRNAs differentially expressed in a qPCR human whole micronome array performed in tissues from endometriosis and control patients. 37 miRNAs were significantly differentially expressed.

Example 1—Elucidation of Mechanisms for Inflammatory Pain and Proliferation in Endometriosis Patients A qPCR human whole micronome array was performed in tissues from endometriosis and control patients. 37 miRNAs were significantly differentially expressed. A TargetScan analysis of the 37 miRNAs led to further investigations of particular genes, with 8 of the miRNAs identified as capable of targeting the 3' UTR of JARID2 with broad conservation (FIGS. 2A-2B).

Figure 3:
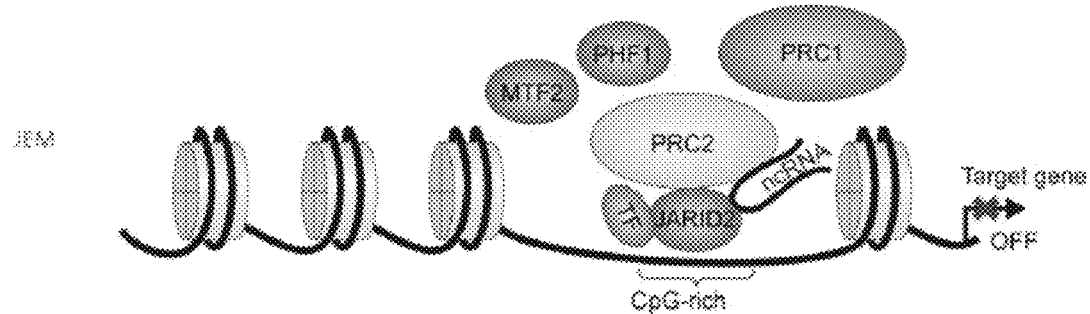
FIG. 3 is another schematic diagram depicting how the mRNA is targeted directly by miR-155 and indirectly by about 20 other miRNAs.
Figure 4:
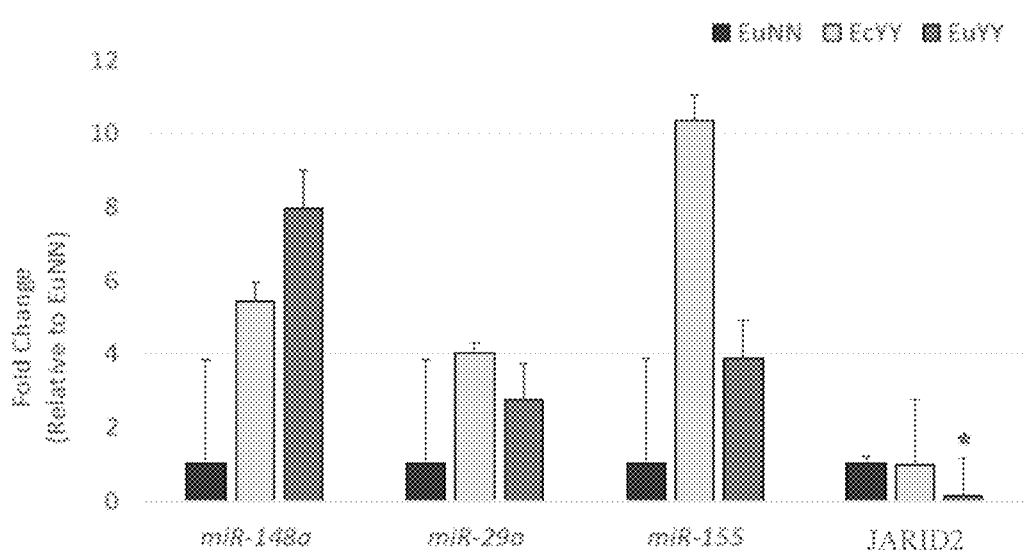
FIG. 4 is a graph showing expression of JARID2 and miRNAs that target JARID2 in patient tissue samples. Compared to control tissues (Eutopic NN n=3), expression of miR-148a, miR-29a, and miR-155 were all higher in endo tissues (both eutopic and ectopic, n=3). JARID2 was significantly underexpressed in eutopic tissues from endo patients when compared to control tissues (*p=0.004). NN—no endometriosis, n pain; YY—endometriosis and pain

As depicted schematically in FIG. 3, mRNA can be targeted directly by miR-155 and indirectly by about 20 other miRNAs. In this regard, FIG. 4 provides results of expression of JARID2 and targeting miRNAs in patient tissues. Specifically, miRNA qPCR assays were used to measure expression of miR-148a, miR-29a, and miR-155, which, among others, target JARID2 (TargetScan, IPA). All three miRNAs were overexpressed in endometriosis (eutopic and ectopic) tissues compared to control tissues (FIG. 4). miR-29a and miR-155 had more pronounced expression in endometriotic lesions than other tissue groups, while miR-148a expression was greatest in EuYY tissues. Compared to control tissues, JARID2 was significantly down-regulated in eutopic endometrium from endometriosis patients (p=0.004).

Example 2—Treatment with Peritoneal Fluid

Figure 5A:
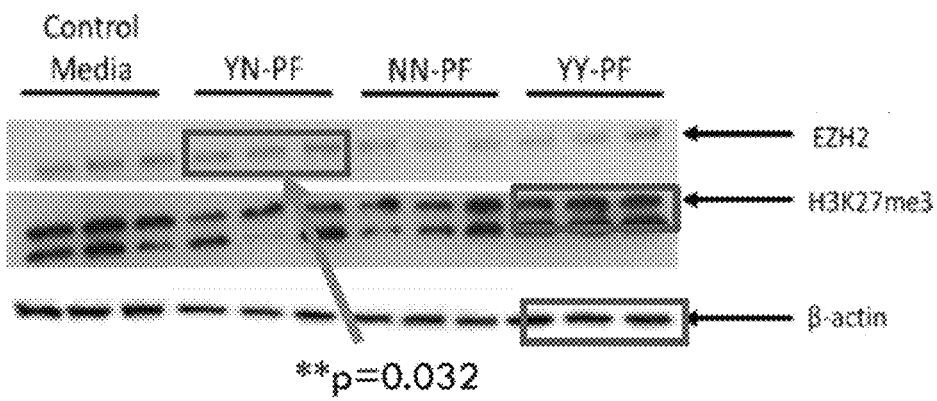
FIG. 5A is a Western blot showing an increase in EZH2 in the presence of 1% PF.
Figure 5B:
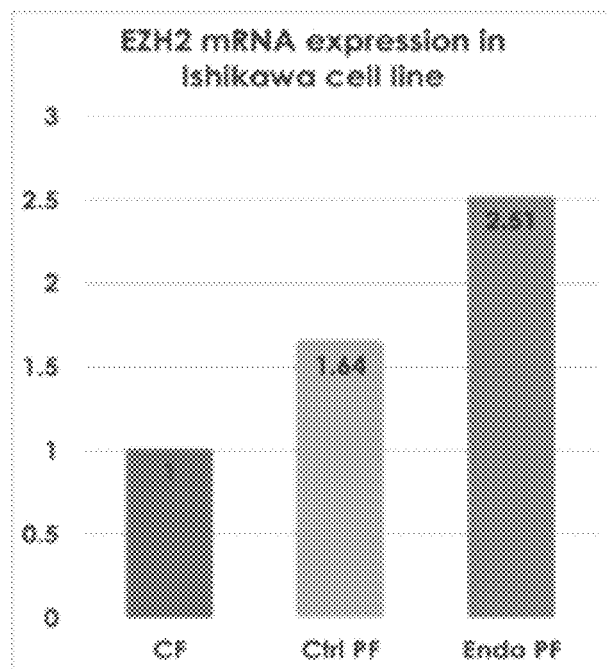
FIG. 5B is a graph charting a 2-3 fold induction in EZH2 mRNA expression in the presence of 1% PF from women with endometriosis.

A 2-3 fold induction in EZH2 mRNA expression in presence of 1% PF from women with endometriosis was observed and is shown in FIG. 5B. Western blot analysis also showed the increase in EZH2 in the presence of 1% PF (FIG. 5A).

Figure 6A:
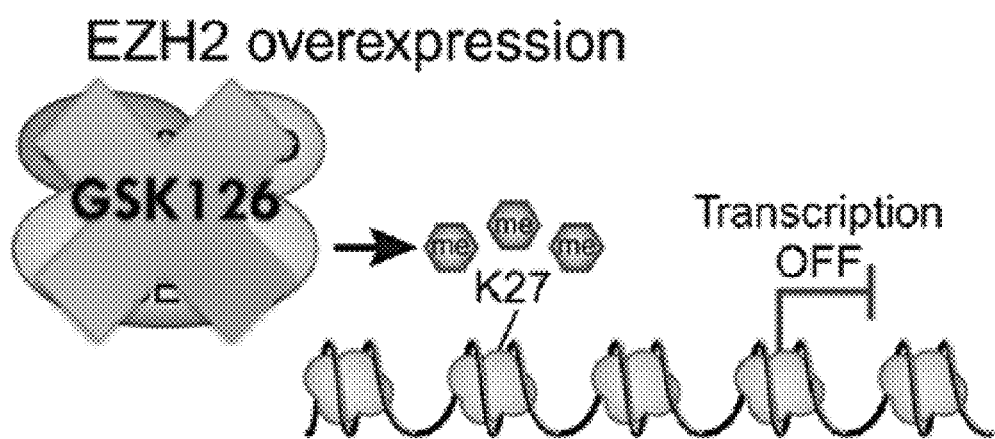
FIG. 6A includes a schematic diagram showing the selectivity of GSK 126 for EZH2.
Figure 6B:
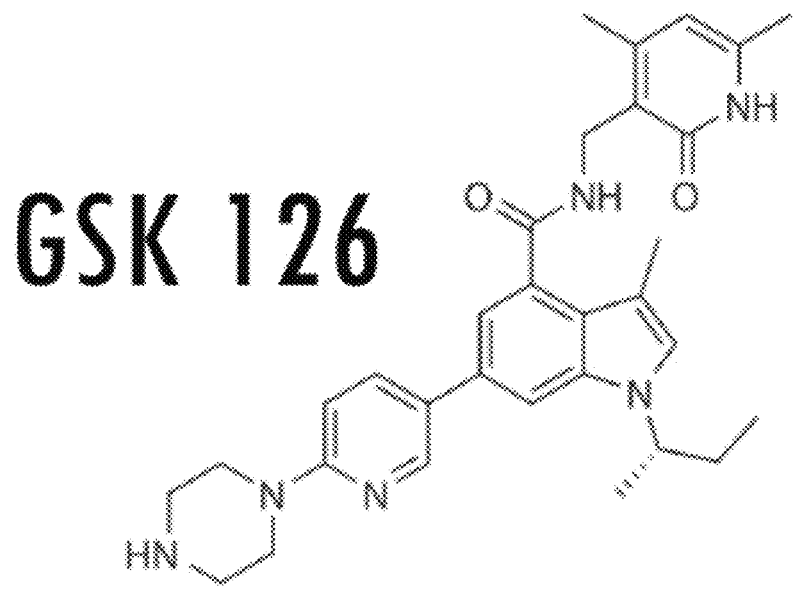
FIG. 6B shows the chemical structure of GSK 126.
Figure 7A:
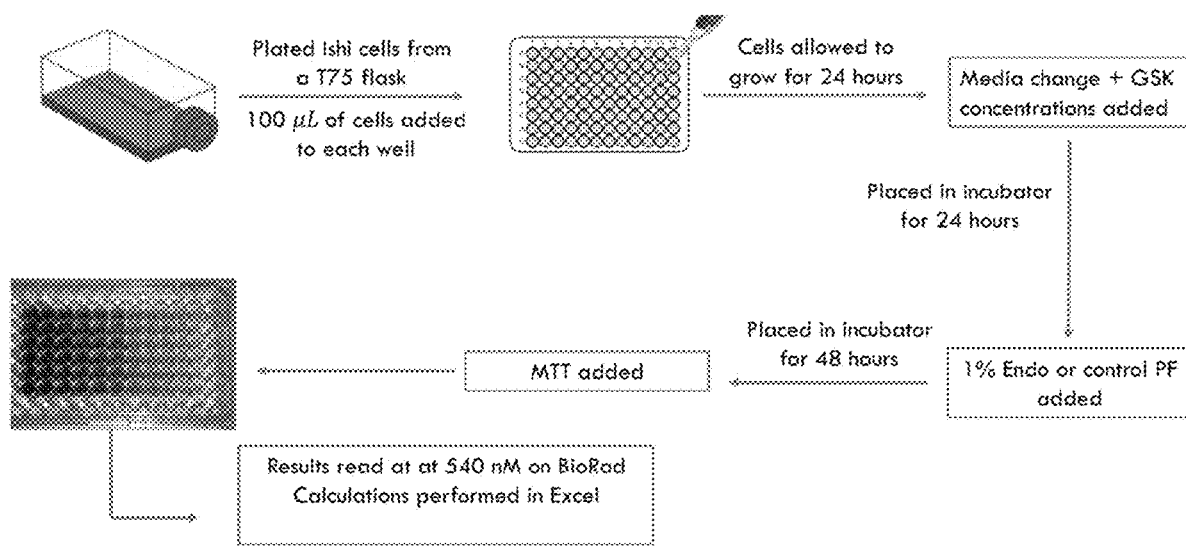
FIG. 7A is a schematic showing an inhibitor study conducted using MTT analysis.
Figure 7B:
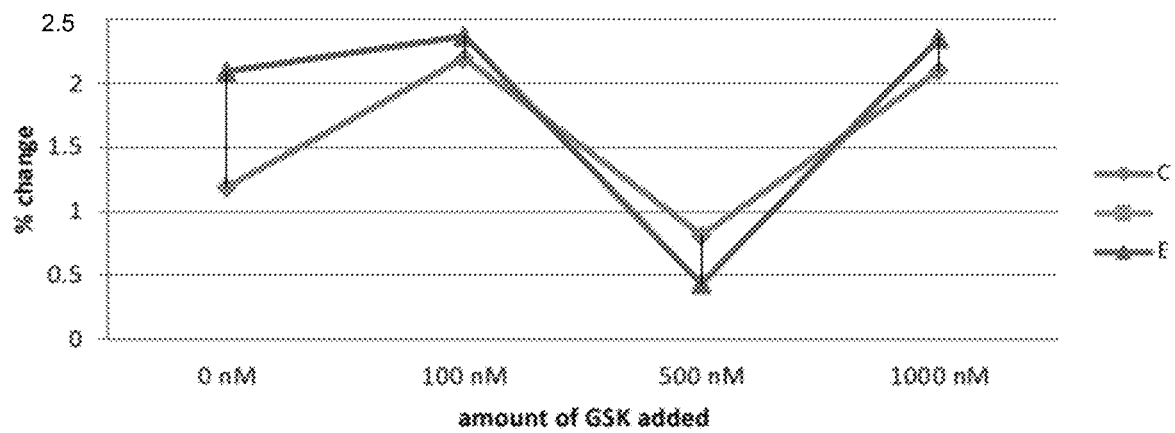
FIG. 7B is a graph charting the change in cell growth of Ishikawa cells treated with GSK 126 and 1% PF.
Figure 7C:
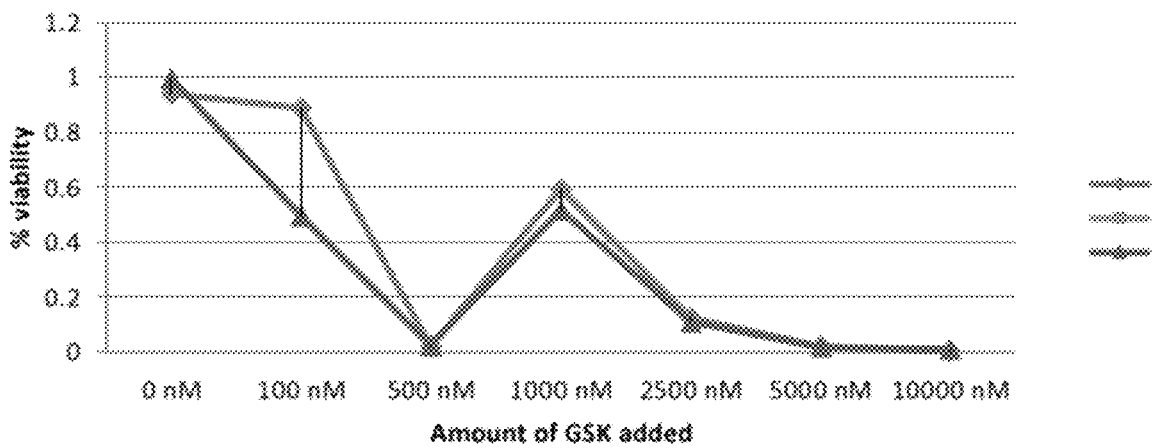
FIG. 7C is a graph charting the percent viability of Ishikawa cells treated with GSK 126 and 1% PF.
Figure 8:
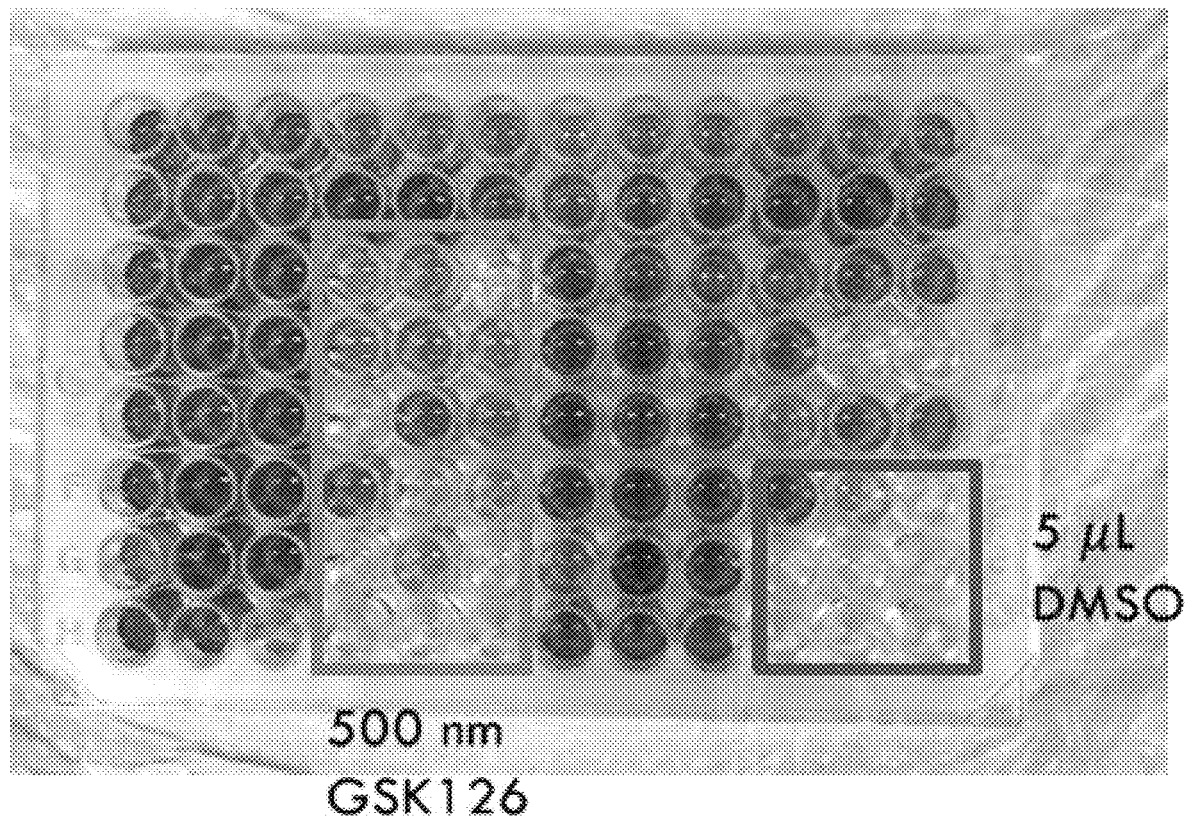
FIG. 8 is an image of a plate showing cells treated with 500 nM GSK 126 and 5 µL DMSO.

GSK 126, the chemical structure of which is shown in FIG. 6B, a selective, S-adenosyl-methionine competitive small molecule inhibitor of EZH2 methyltransferase activity, was investigated as described in further detail below. It included a Ki=0.57 nM and an $IC_{50}$=9.9 mM. It was more than 1000 fold selective for EZH2 over other histone methyltransferases, including both SET-domain-containing and non-SET domain-containing methyltransferases, as shown schematically in FIG. 6A. GSK 126 was also shown to inhibit global H2K37 trimethylation levels to reactivate silenced PRC2 genes. In this regard, an inhibitor study using MTT analysis was conducted according to the schematic of FIG. 7A. Various doses of GSK126 were tested on Ishikawa cells in the presence of PF: 100 nM, 500 nM, 1 μM, 2.5 μM, 5 μM, and 10 μM in DMSO. Cell growth and viability of cells was evaluated rather than just EZH2 expression. (FIGS. 7B-7C) 1 mM and 0.1 mM solutions of GSK126 were also created from serial dilutions of 10 mM GSK126. Of note, very little proliferation seen in cells, with a dip in viability at 500 nM (FIG. 8). It was somewhat unclear, however, whether that the effect of the drug as the volume of the vehicle (DMSO) could have impacted the results.

Previous studies suggested a complex interplay between epigenetic mediators, PRC2 complex, miR-155-5p and the inflammatory mediator FOXP3. Accordingly, additional studies were undertaken to investigate whether the imbalance in this cross-talk triggered inflammatory responses and nociception in endometriosis between these-mediators in patient tissues and an endometriosis cell model.

Example 3—PRC2 and FOXP3 Expression in Patient Tissues

Figures 9A, 9B, 9C:
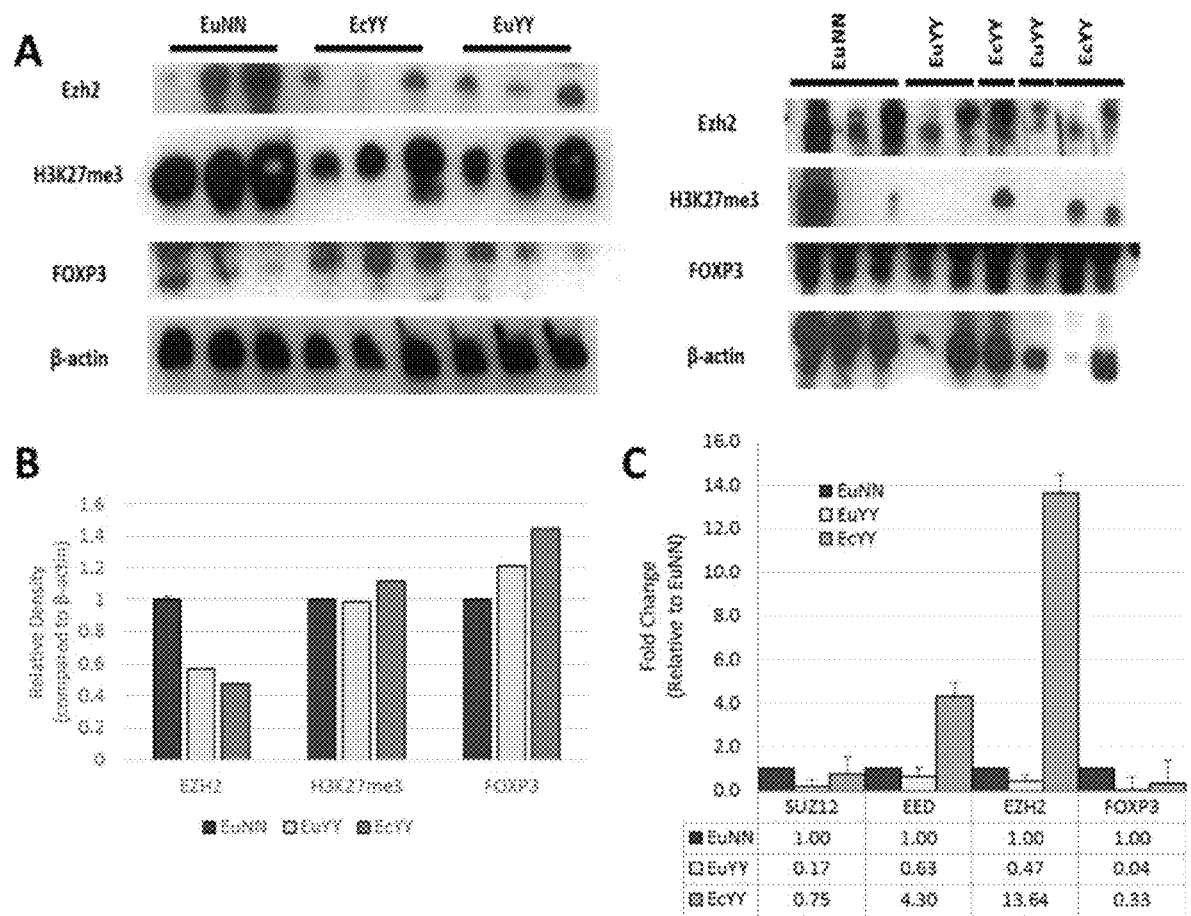
FIGS. 9A-9C show protein and gene expression of key epigenetic mediators in endometriosis and control tissues.

Protein levels of EZH2, H3K27me3, and FOXP3 in EuNN (Eutopic tissue, endo-), EuYY (eutopic tissue, endo+), and EcYY (ectopic tissue, endo+) tissues (n=6) are shown in the Western blot in FIG. 9A. No significant difference was seen between the mean density of endo tissue and control tissue bands (FIG. 9B). qPCR was used to determine the expression of PRC2 components SUZ12, EED, and EZH2, as well as FOXP3 (FIG. 9C). When compared to the control tissues, expression of all four genes was lower in eutopic tissue from endometriosis patients (EuYY). In contrast, ectopic tissues expressed higher levels of EED and EZH2 than control tissues, with a p-value of 0.06.

Example 4—Epigenetic Expression in an Endo Cell Model

Figures 10A, 10B, 10C:
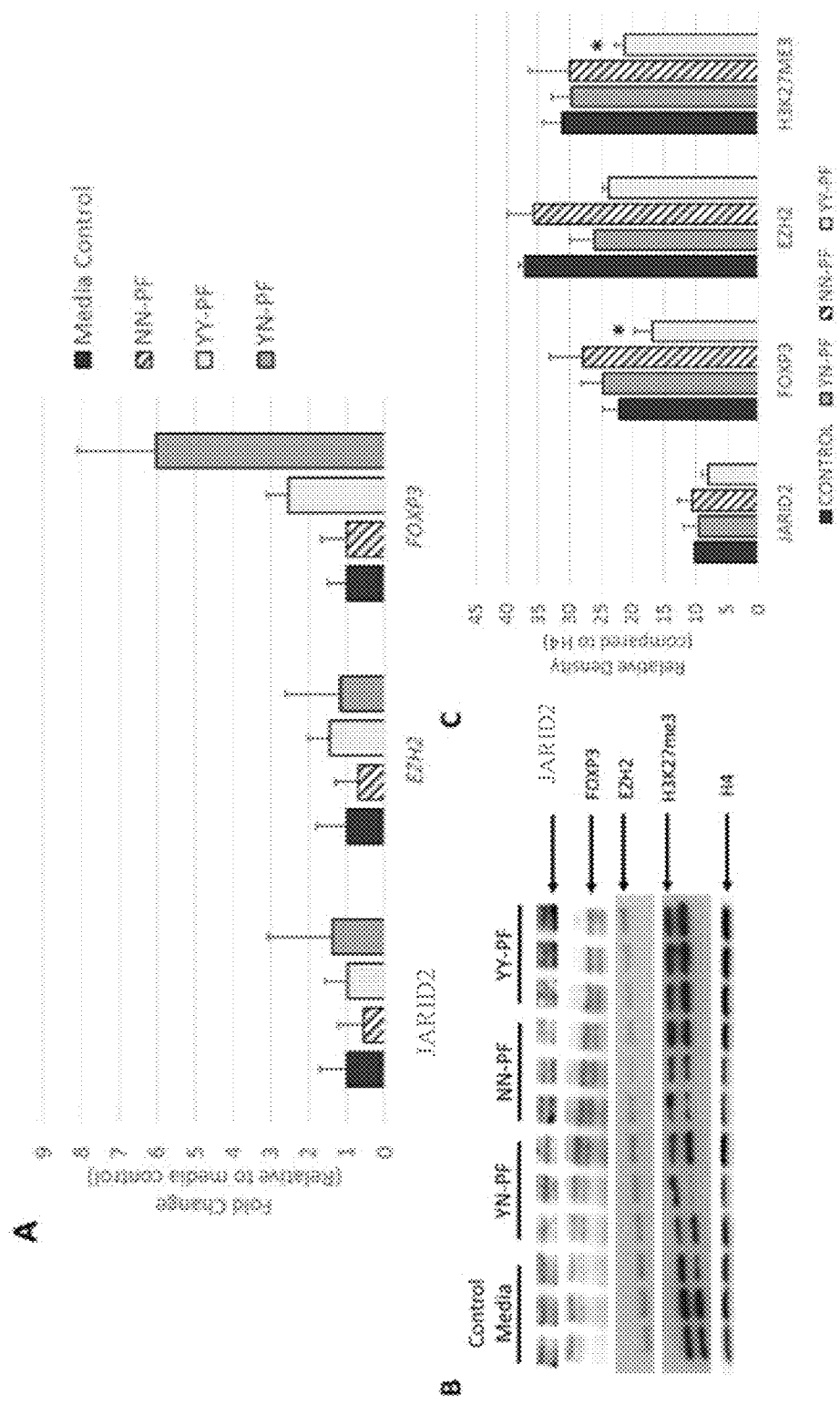
FIG. 10A is a graph showing mRNA expression in an endometriosis cell model of JARID2, EZH2, and FOXP3 in cells treated with NN-PF (n=6), YY-PF (n=5), and YN-PF (n=3), relative to expression in a media control (p>0.05)
FIG. 10B shows Western blots for JARID2, FOXP3, EZH2, and H3K27me3 in PF-treated cells. Arrows indicate the appropriate row of bands.
FIG. 10C is a graph showing the densitometric analysis of Western blots. Relative protein expression of JARID2, EZH2, and FOXP3 in PF-treated cells was calculated in relation to a media control. FOXP3 expression was 0.763-fold lower in YY-PF than in control media; and H3K27me3 levels were 0.679-fold lower in YY-PF than in media control; p<0.05; NN—no endometriosis, no pain; YY—endometriosis and pain FIG. 11 includes graphs showing mRNA levels in cells transfected with a miR-155 mimic and antagonist. Transfection with a miR-155 mimic had little effect on JARID2 expression in PF-treated cells (p>0.05), but seemed to increase FOXP3 expression in cells treated with control PF. Compared to control media, the miR-155 antagonist significantly decreased JARID2 expression in cells treated with YY-PF (*p=0.017).

Protein and mRNA expression of epigenetic regulators were measured in endometrial cells treated with peritoneal fluid from women with and without endometriosis and pain (FIGS. 10A-10C). Cells treated with endo Peritoneal Fluid (PF) (YN-PF and YY-PF) had increased JARID2, EZH2, and FOXP3 mRNA expression compared to media control. NN-PF had no such induction, where +endo/+pain (YY-PF), +endo/-pain (YN-PF), and -endo/-pain (NN-PF, "control fluid"). The corresponding protein expression was similar among the PF treatments. Despite the significant decrease in EZH2 upon YN-PF treatment compared to media control (0.66 fold change, p=0.032), there was no such discernable difference when it was compared to NN-PF treatment. FOXP3 protein expression was significantly lower (0.763-fold) in YY-PF treated cells when compared to NN-PF treated cells. The double band seen in FIG. 10B could be explained by post-translational modifications to its regulatory elements. To test for this, calf intestinal phosphatase (CIP) could be added to the samples, resulting in fused bands or elimination of the band representing phosphorylation. Trimethylation of H3K27 was also significantly less prevalent in YY-PF treated cells (0.679-fold). Based on the molecular weight of the modification (about 17 kDa), the top bands were measured for densitometry.

Example 5—miR-155 Regulates PRC2 Complex

Figure 11:
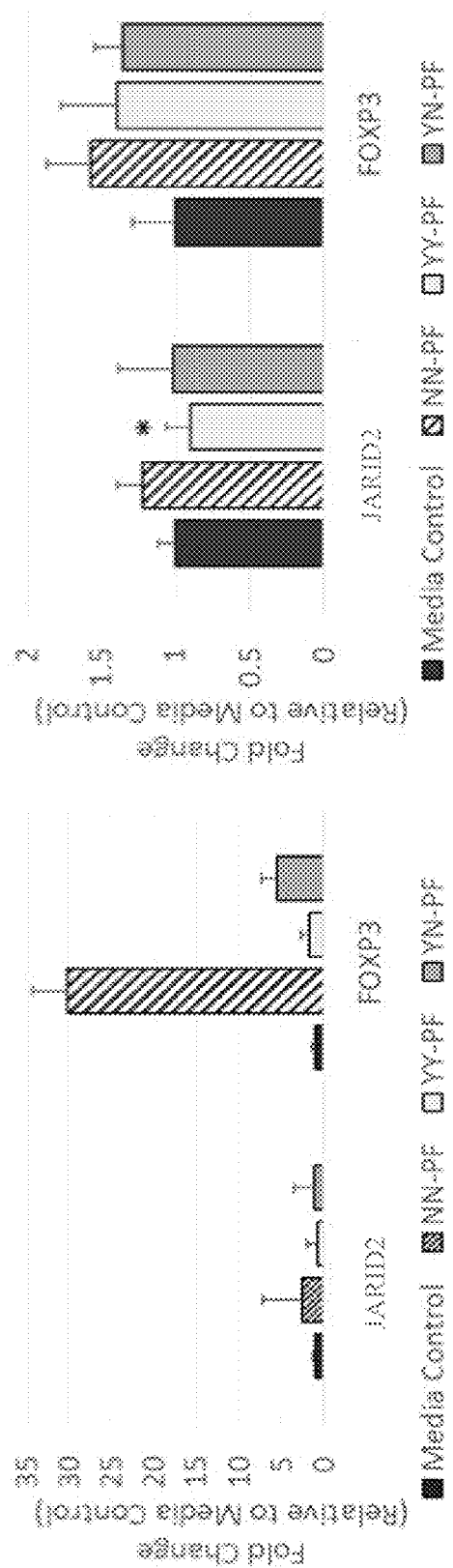

The expression of JARID2 and the PRC2 complex was determined in endometrial cells transfected with a miR-155 mimic or antagonist FIG. 11. The miR-155 mimic had minimal effect on JARID2 protein expression in PF-treated cells (p>0.05), but seemed to increase FOXP3 expression in cells treated with control PF (FIG. 11, left panel). The miR-155 inhibitor significantly decreased JARID2 protein expression in cells treated with YY-PF (p=0.0172. FIG. 11, right panel).

Figures 12A, 12B:
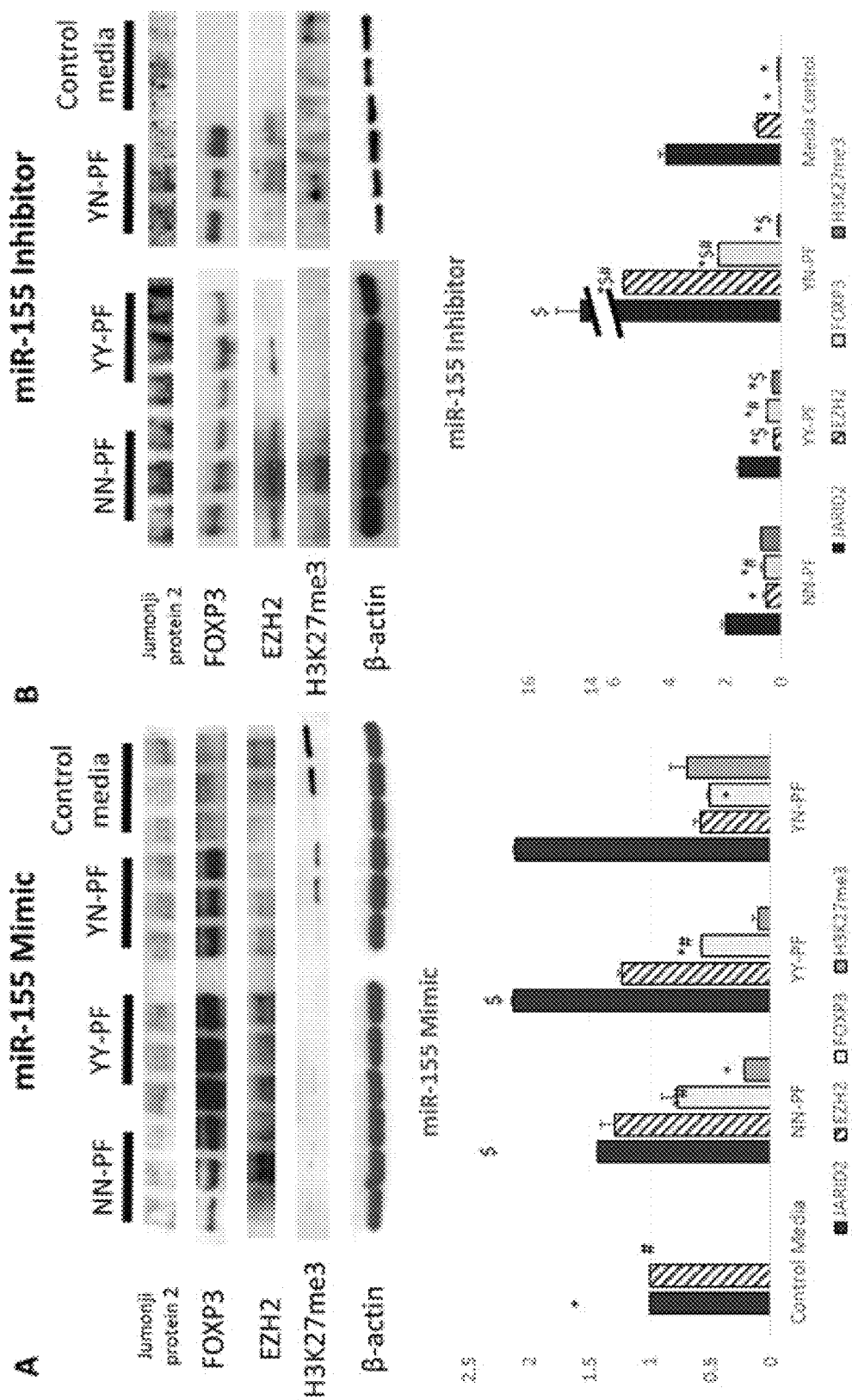
FIG. 12A is a Western Blot and graph showing that transfection with a miR-155 mimic resulted in significantly higher JARID2 expression in endo PF-treated cells (n=3) compared to control PF-treated cells (n=3)(YY-PF p=0.005, YN-PF p=0.002) and lower FOXP3 expression in all PF-treated cells compared to media control cells transfected with miR-155 mimic (NN-PF p=0.0112, YY-PF p=0.0002, YN-PF p=0.0005.
FIG. 12B is a Western Blot and graph showing that transfection with a miR-155 inhibitor resulted in significantly higher JARID2 expression in YN-PF treated cells compared to NN-PF treated cells (p<0.001). EZH2 expression was lower than control media in NN-PF and YY-PF treated cells but higher in YN-PF treated cells (NN-PF p=0.053, YY-PF p=0.006, YN-PF p=0.026). Compared to the media control transfected with miR-155 antagonist, the expression of FOXP3 was significantly higher in all PF-treated cells (NN-PF p<0.001, YY-PF, p=0.006, YN-PF p<0.001). H3K27me3 was less prevalent in endometriosis PF-treated cells compared to NN-PF treated cells (YY-PF p=0.025, YN-PF p<0.001). *Significant difference (p<0.05) in mean compared to control media, $Significant difference (p<0.05) in mean compared to NN-PF, #Significant difference (p<0.05) in mean compared to control media with mimic/inhibitor.

Overexpression of miR-155 resulted in significantly higher JARID2 expression in endo PF-treated cells compared to control PF-treated cells (YY-PF p=0.005, YN-PF p=0.002) (FIG. 12A). FOXP3 expression was significantly lower in all PF-treated cells than media control cells transfected with miR-155 mimic (NN-PF p=0.0112, YY-PF p=0.0002, YN-PF p=0.0005). Inhibition of miR-155 resulted in significantly higher JARID2 expression in YN-PF treated cells compared to NN-PF treated cells (p<0.001) (FIG. 12B). EZH2 expression was lower than control media in NN-PF and YY-PF treated cells but higher in YN-PF treated cells (NN-PF p=0.053, YY-PF p=0.006, YN-PF p=0.026). Compared to the media control transfected with miR-155 antagonist, the expression of FOXP3 was significantly higher in all PF-treated cells (NN-PF p<0.001, YY-PF, p=0.006, YN-PF p<0.00l). Trimethylation of H3K27 was less prevalent in endo PF-treated cells compared to NN-PF treated cells (YY-PF p=0.025, YN-PF p<0.001).

Example 6—Epigenetic Regulation of FOXP3

Figure 13:
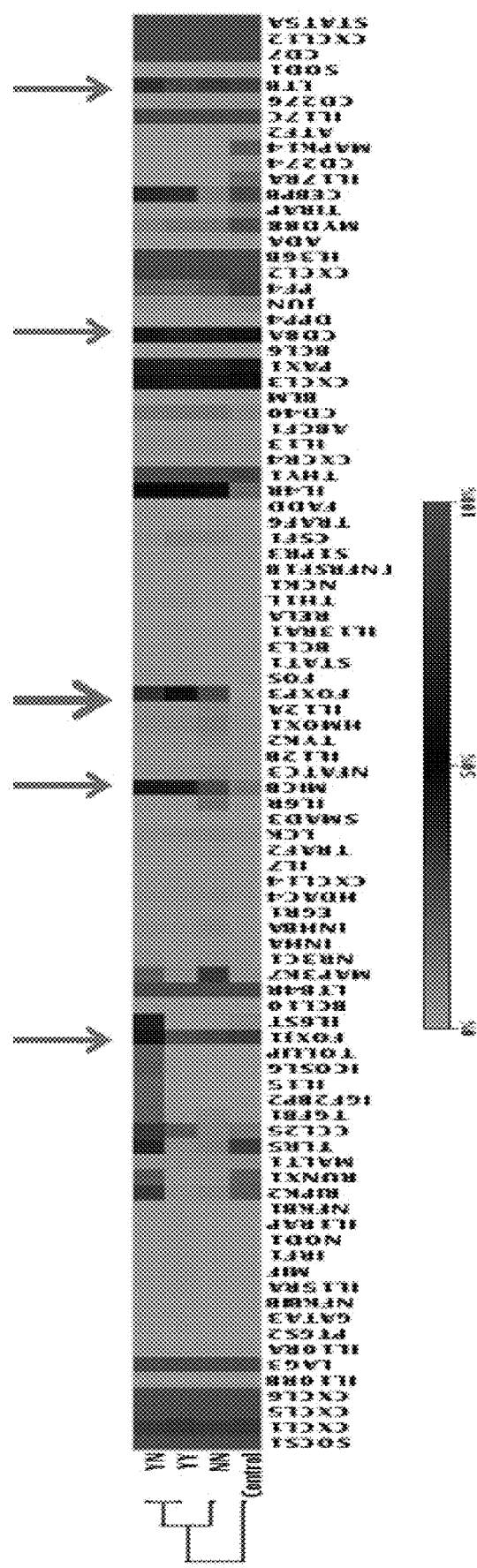
FIG. 13 is a heat map showing DNA methylation trends in PF-treated cells on promoters of genes associated with autoimmunity and inflammation. Treatment groups with green shades have lower methylation fractions than those with red shades. Of interest is FOXP3, which has been deemed a tumor suppressor gene. YY-PF: M=56.67%; YN-PF: M=33.73%; NN-PF: M=25.54%; Control media: M=0.23%.

Global DNA methylation array to assess promoter methylation patterns showed changes in genes involved in inflammation and autoimmunity. The heat map in FIG. 13 presents a range (from 0 to 100) of "M", the fraction of input genomic DNA containing 2+ methylated CpG sites in the targeted region of a gene. Based on the fold changes (p>0.05 in all instances), the following five genes were identified as being impacted by DNA methylation: Forkhead box protein J1 (FOXJ1), MHC class I polypeptide-related sequence B (MICB), forkhead box P3 (FOXP3), Cluster of Differentiation 8a (CD8A), and Lymphotoxin Beta (LTB). All genes, except CD8A, had an increased methylation pattern in cells treated with endo PF (YN and YY) compared to NN-PF and the media control. FOXP3 M values were 56.67% in YY-PF treated cells, 25.54% in NN-PF treated cells, 33.73% in YN-PF treated cells, and 0.23% in control media. Bisulfite sequencing will be used in the future to better understand the methylation patterns of sample DNA.

Example 7—JARID2 Regulates PRC2 Target Genes

Figure 14:
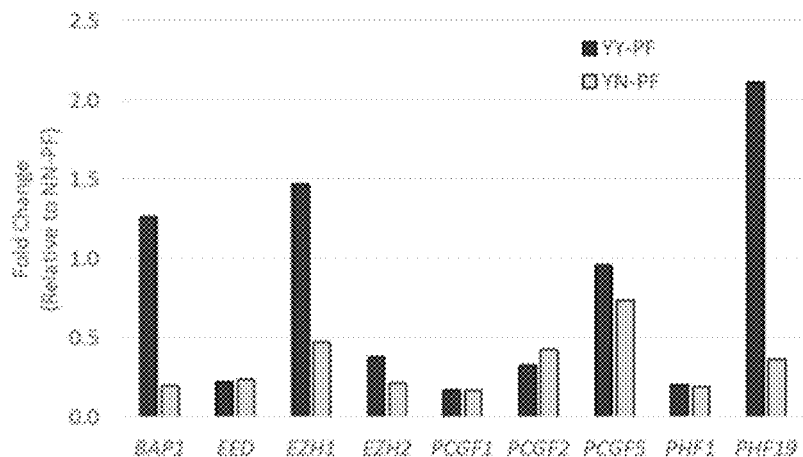
FIG. 14 is a graph showing chromatin immunoprecipitation to analyze interactions between JARID2 and genes associated with the polycomb and trithorax complexes, normalized to IgG. Fold change values represent the ratio of enrichment/binding of JARID2 to various genes in endo PF-treated cells (n=3) to enrichment in control PF-treated cells (n=3). Generally, increased enrichment was seen on genes in the presence of YY-PF compared to YN-PF. However, fold change indicated that both endometriosis conditions resulted in lower enrichment compared to control PF. p>0.05. BAP1: BRCA1 associated protein-1; EED: Embryonic ectoderm development; EZH1: Enhancer of zeste homolog 1; EZH2: Enhancer of zeste homolog 2; PCGF1: Polycomb group ring finger 1; PCGF2: Polycomb group ring finger 2; PCGF5: Polycomb group ring finger 5; PHF1: PHD finger protein 1; PHF19: PHD finger protein 19.

To determine the epigenomic targets of JARID2 ChIP was performed using JARID2 antibody followed by promoter array of genes associated with polycomb and trithorax complexes in cells treated with PF (Table 2). Generally, there was less enrichment of the genes (BAP1, EED, EZH1, EZH2, PCGF1, PCGF2, PCGF5, PHF1, PHF19) when cells were treated with endo PF. FIG. 14 provides a graphical representation of genes with notable differences in YY-PF and YN-PF, when compared to NN-PF. The enrichment of EZH2 by JARID2 was lower in endo PF-treated cells compared to NN-PF treated cells. EZH1, a polycomb enzyme which is responsible for mono-, di-, or tri-methylation of H3K27, showed greater enrichment by JARID2 in YY-PF treated cells than NN-PF treated cells. PCGF represents the polycomb group ring finger genes, which had similar fold change values in both endo treatment groups. For all data, p>0.05, likely due in part to small sample size.

TABLE 2

EpiTect ChIP qPCR array was used to measure enrichment of JARID2 by an array of epigenetic genes. Fold change values for YY-PF and YN-PF treated cells are shown in comparison to NN-PF treated cells. For all fold change values, p > 0.05.
JARID2 protein enrichment in PF-treated cells.

| Symbol | Gene Name | Fold Change (relative to NN-PF) | |
|---|---|---|---|
| | | YY-PF | YN-PF |
| AEBP2 | AE binding protein 2 | 1.6764 | 0.7852 |
| ARID1A | AT rich interactive domain 1A (SWI-like) | 0.4693 | 0.4634 |
| ARID1B | AT rich interactive domain 1B (SWI1-like) | 0.9723 | 0.5931 |
| ASH2L | Ash2 (absent, small, or homeotic)-like (*Drosophila*) | 0.9301 | 1.5583 |
| ASXL1 | Additional sex combs like 1 (*Drosophila*) | 2.4314 | 0.0898 |
| ASXL2 | Additional sex combs like 2 (*Drosophila*) | 0.2951 | 0.2665 |
| ASXL3 | Additional sex combs like 3 (*Drosophila*) | 0.0160 | 0.0152 |
| BAP1 | BRCA1 associated protein-1 (ubiquitin carboxy-terminal hydrolase) | 1.2660 | 0.1986 |
| BMI1 | BMI1 polycomb ring finger oncogene | 0.1011 | 0.1393 |
| CBX1 | Chromobox homolog 1 | 1.4018 | 0.5735 |
| CBX2 | Chromobox homolog 2 | 0.1616 | 0.0870 |
| CBX3 | Chromobox homolog 3 | 0.8390 | 0.4244 |
| CBX4 | Chromobox homolog 4 | 0.1857 | 0.1730 |
| CBX5 | Chromobox homolog 5 | 0.5370 | 0.3638 |
| CBX7 | Chromobox homolog 7 | 0.8786 | 0.4784 |
| CBX8 | Chromobox homolog 8 | 2.8055 | 1.6042 |
| CTBP2 | C-terminal binding protein 2 | 0.5714 | 1.2007 |
| CXXC1 | CXXC finger protein 1 | 1.1725 | 0.1560 |
| DNMT1 | DNA (cytosine-5-)-methyltransferase 1 | 0.2437 | 0.6107 |
| DNMT3A | DNA (cytosine 5-)-methyltransferase 3 alpha | 0.7087 | 0.4211 |
| DNMT3B | DNA (cytosine 5-)-methyltransferase 3 beta | 0.0853 | 0.1309 |
| DNMT3L | DNA (cytosine 5-)-methyltransferase 3 like | 0.1152 | 0.5191 |
| E2F6 | E2F transcription factor 6 | 0.7287 | 0.2305 |
| EED | Embryonic ectoderm development | 0.2229 | 0.2396 |
| EPC1 | Enhancer of polycomb homolog 1 (*Drosophila*) | 0.1098 | 0.1849 |
| EPC2 | Enhancer of polycomb homolog 2 (*Drosophila*) | 0.1692 | 0.1165 |
| EZH1 | Enhancer of zeste homolog 1 (*Drosophila*) | 1.4713 | 0.4691 |
| EZH2 | Enhancer of zeste homolog 2 (*Drosophila*) | 0.3789 | 0.2118 |
| HLTF | Helicase-like transcription factor | 0.4687 | 0.7129 |
| HTT | Huntingtin | 1.5628 | 0.1519 |
| INO80 | INO80 homolog (*S. cerevisiae*) | 2.1467 | 1.4215 |
| INO80B | INO80 complex subunit B | 0.7977 | 0.3877 |
| INO80C | INO80 complex subunit C | 0.2878 | 0.1857 |
| INO80D | INO80 complex subunit D | 2.0547 | 0.3405 |
| JARID2 | Jumonji, AT rich interactive domain 2 | 1.4335 | 1.1251 |
| KDM2B | Lysine (K)-specific demethylase 2B | 2.0734 | 0.2742 |
| KDM5D | Lysine (K)-specific demethylase 5D | 0.6292 | 0.3758 |
| L3MBTL.2 | L(3)mbt-like 2 (*Drosophila*) | 0.8336 | 0.9427 |
| LARP7 | La ribonucleoprotein domain family, member 7 | 1.7783 | 0.6885 |
| MBTD1 | Mbt domain containing 1 | 0.6876 | 0.3907 |
| MLL2 | N/A | 1.5074 | 2.3571 |
| MLL3 | N/A | 2.2835 | 0.8004 |
| MLL4 | N/A | 0.5182 | 0.5166 |
| MLL5 | N/A | 0.9117 | 0.4559 |
| MOV10 | Mov10, Moloney leukemia virus 10, homolog (mouse) | 1.2929 | 0.4274 |
| MTF2 | Metal response element binding transcription factor 2 | 2.7750 | 0.5744 |
| PBRM1 | Polybromo 1 | 0.5870 | 0.9439 |
| PCGF1 | Polycomb group ring finger 1 | 0.1706 | 0.1668 |
| PCGF2 | Polycomb group ring finger 2 | 0.3269 | 0.4222 |
| PCGF5 | Polycomb group ring finger 5 | 0.9582 | 0.7378 |
| PHC1 | Polyhomeotic homolog 1 (*Drosophila*) | 0.3971 | 0.8962 |
| PHC2 | Polyhomeotic homolog 2 (*Drosophila*) | 1.3555 | 0.6890 |
| PHC3 | Polyhomeotic homolog 3 (*Drosophila*) | 0.2112 | 0.3125 |
| PHF1 | PHD finger protein 1 | 0.2040 | 0.1897 |
| PHF19 | PHD finger protein 19 | 2.1147 | 0.3604 |
| PPP1CC | Protein phosphatase 1, catalytic subunit, gama isozyme | 0.1204 | 0.2635 |
| PPP1R8 | Protein phosphatase 1, regulatory (inhibitor) subunit 8 | 0.7383 | 0.2492 |
| RBBP4 | Retinoblastoma binding protein 4 | 0.2471 | 1.0525 |
| RBBP5 | Retinoblastoma binding protein 5 | 0.1376 | 0.0443 |
| RBBP7 | Retinoblastoma binding protein 7 | 0.5166 | 0.6042 |
| RBP2 | Retinol binding protein 2, cellular | 0.3213 | 1.1246 |
| RING1 | Ring finger protein 1 | 0.4850 | 0.7653 |
| RNASEL | Ribonuclease L (2',5'-oligoisoadenylate synthetase-dependent) | 35.2393 | 1.4799 |
| RNF2 | Ring finger protein 2 | 0.1071 | 0.9140 |
| RYBP | RING1 and YY1 binding protein | 0.6744 | 0.4217 |
| SCMH1 | Sex comb on midleg homolog 1 (*Drosophila*) | 0.5102 | 0.6293 |
| SCML2 | Sex comb on midleg-like 2 (*Drosophila*) | 1.1876 | 0.4366 |
| SIRT1 | Sirtuin 1 | 0.7959 | 0.5408 |

TABLE 2-continued

EpiTect ChIP qPCR array was used to measure enrichment of JARID2 by an array of epigenetic genes. Fold change values for YY-PF and YN-PF treated cells are shown in comparison to NN-PF treated cells. For all fold change values, p > 0.05.
JARID2 protein enrichment in PF-treated cells.

| | | Fold Change (relative to NN-PF) | |
|---|---|---|---|
| Symbol | Gene Name | YY-PF | YN-PF |
| SMARCA1 | SW1/SNF related, matrix associated, actin dependent regulator of chromatin, subfamily a, member 1 | 0.0175 | 0.0139 |
| SMARCA2 | SW1/SNF related, matrix associated, actin dependent regulator of chromatin, subfamily a, member 2 | 1.0762 | 2.2627 |
| SMARCA4 | SW1/SNF related, matrix associated, actin dependent regulator of chromatin, subfamily a, member 4 | 0.3709 | 1.0019 |
| SMARCA5 | SW1/SNF related, matrix associated, actin dependent regulator of chromatin, subfamily a, member 5 | 0.0006 | 0.0000 |
| SMARCB1 | SW1/SNF related, matrix associated, actin dependent regulator of chromatin, subfamily b, member 1 | 0.6263 | 1.5164 |
| SMARCC1 | SW1/SNF related, matrix associated, actin dependent regulator of chromatin, subfamily c, member 1 | 0.2038 | 0.4334 |
| SMARCC2 | SW1/SNF related, matrix associated, actin dependent regulator of chromatin, subfamily c, member 2 | 1.2640 | 0.4916 |
| SNAI1 | Snail homolog 1 (*Drosophila*) | 8.6431 | 0.9088 |
| TRIM27 | Tripartite motif containing 27 | 1.0677 | 0.7358 |
| USP11 | Ubiquitin specific peptidase 11 | 4.0273 | 0.0308 |
| USP7 | Ubiquitin specific peptidase 7 (herpes virus-associated) | 1.9792 | 1.3341 |
| WDR5 | WD repeat domain 5 | 0.3646 | 0.1782 |
| YAF2 | YY1 associated factor 2 | 1.3949 | 2.0025 |
| YY1AP1 | YY1 associated protein 1 | 1.0428 | 0.4460 |
| YY2 | YY2 transcription factor | 0.6151 | 1.3238 |
| ZBTB16 | Zinc finger and BTB domain containing 16 | 0.2603 | 2.2601 |

Discussion of Examples 1-7

Research identifying underlying mechanisms of pain experienced by endometriosis patients has been ongoing. This study stemmed from investigations into the miRNA profile of endometriosis tissues and peritoneal fluid (PF). Nineteen percent of differentially expressed miRNAs in endometriosis tissues targeted JARID2. Despite the global downregulation seen in the micronome of endometriotic tissues, miRNAs that targeted JARID2 were highly expressed in the eutopic tissues of endometriosis patients with pain. The overexpression of miR-148a, miR-29a, and miR-155 in endo tissues (FIG. 4) supported this theory. Although little to no difference in PRC2 protein expression was seen among tissues, there was a noticeable trend in overexpression of corresponding genes in ectopic tissues from endometriosis patients, particularly in EZH2 (p=0.06). This correlates with the findings of Colon-Caraballo and colleagues and supports the characterization of EZH2 as a contributor to transcriptional repression and progression of the disease. FOXP3 was present in lesser amounts in endo tissues compared to control tissues. FOXP3 is known for its role as a tumor suppressor and the tendency for inflammation to repress its expression.

Although miR-155 was not originally identified based on the micronome array (p>0.05), its relationship with JARID2 has recently drawn the attention of researchers in the field of inflammatory disease. miR-155 seems to play a key intermediary target that regulates the crosstalk between JARID2 and PRC2. Hence miR-155 is a potential therapeutic target. The above-described study explored the role of miR-155 in endometriosis by transfecting PF treated cells with a miR-155 mimic or antagonist. Despite the knowledge that FOXP3 targets miR-155, overexpression of miR-155 in PF-treated cells resulted in little to no difference in FOXP3 expression among the three treatment groups. However, blocking miR-155 resulted in significant overexpression of FOXP3 in YN-PF treated cells. The effect of altering miR-155 on JARID2 was also interesting. Compared to control PF-treated cells, cells treated with endo PF overexpressed JARID2 when transfected with the miR-155 mimic. When transfected with the miR-155 inhibitor, only cells treated with YN-PF overexpressed JARID2 compared to control PF treatments. These results were unexpected and suggest that the miRNA regulation of FOXP3 and JARID2 is not sufficient to alter expression. Other transcription factors and/or epigenetic mediators could play a role in aberrant expression in endometriosis. Knocking down miR-155 provided the most insight into the mechanism. While the presence of pain seemed to contribute to the downstream repression of EZH2, the repression of the histone modification was seen in cells treated with both endo PFs in comparison to NN-PF treated cells, suggesting that this interaction may be related to the presence of endometriosis independent of the pain symptom.

Methylation of the FOXP3 promoter could be partly responsible based on the trend of increased methylation in cells treated with PF from endo patients, particularly those reporting pain. FOXP3 expression in endo PF-treated cells trended lower than that of cells treated with control PF and protein expression varied very little among the treatment groups. EZH2 expression was significantly lower in cells treated with YN-PF than in the media control but no difference was seen among PF treatment groups. The benefit of studying these epigenetic mediators in tissues and treated cells provided the ability to compare short-term and long-term effects of peritoneal fluid on endometrial cells.

ChIP-qPCR was used to better understand the role that JARID2 plays in endometriosis-associated pain. By observing how it binds to regulatory elements of various genes, a sense of how the mechanisms described above differ between PF from patients with pain to those without was gained. The data presented in FIG. 14 indicated that the JARID2 interaction with EZH2 may not be as strong in a "painful" situation as it is with EZH1, which can also methylate H3K27 to contribute to transcriptional repression. Although it is typically associated with active domains, EZH1 can actually achieve repressive results similar to EZH2 via additional histone modifications. It is interesting to note that, in general, binding of JARID2 to these genes was less likely to occur in cells exposed to endo PF compared to control PF. One exception was PHF19, where enrichment appeared to be greater in cells treated with YY-PF compared to both NN-PF and YN-PF ($p>0.05$). PHF19 has the ability to bind H3K36me3, which allowed it to act as a recruiter for the PCR2 complex, suggesting that another mechanism may be at play in transcriptional repression. PHF19 has also been deemed a role player in the switch from proliferative to invasive states in melanoma cells.

The findings presented here, as summarized in FIG. 1, provide potential mechanisms for inflammatory pain and proliferation in endometriosis patients. This opens the door for novel therapies such as EZH2 inhibitors and miRNA mimics/antagonists. Future studies will test such therapies (e.g. GSK126 and sulforaphane, established as anti-inflammatory agents) in cell and animal models of endometriosis. Although histone demethylases are thought to be ineffective against Jumonji protein 2 due to its lack of true demethylase activity, additional investigations into the role of Jumonji protein 2 in endometriosis could uncover alternative options to therapeutically regulate it.

Materials and Methods for Example 8

Peritoneal Fluid. The study was IRB approved by the HIC of Marshall University. Peritoneal fluid (PF) was collected from patients with and without endometriosis during laparoscopy surgery for endometriosis or tubal ligation.

Figure 15:
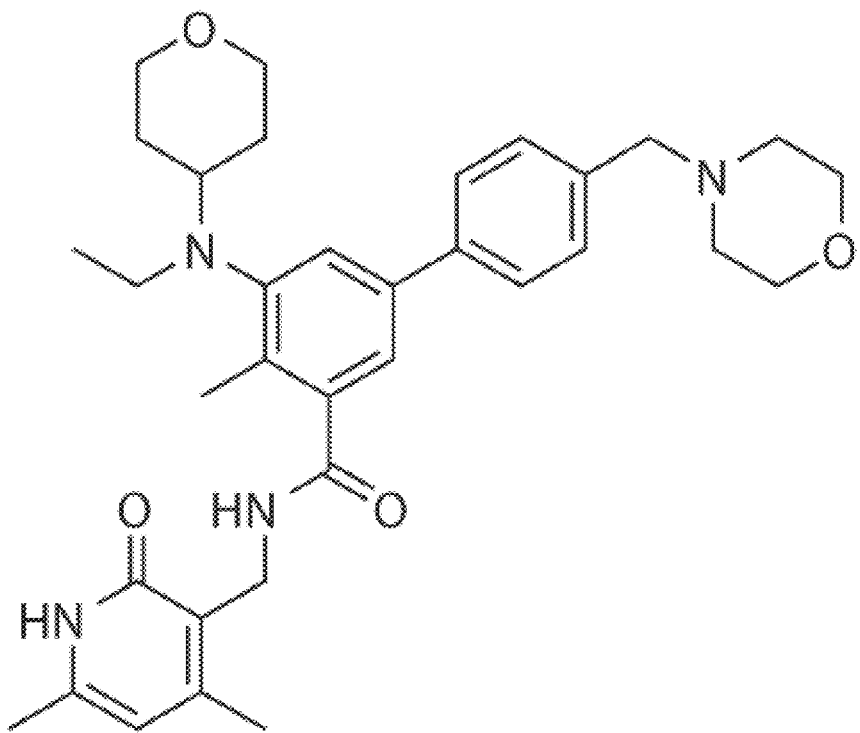
FIG. 15 shows the molecular structure for EPZ-6438 ($K_1$=2.5 nM, $IC_{50}$=11 mM).

Cell treatment. Ishikawa cells (human endometrial cell line) or EOOF5 cells (primary endometrial cells from a patient without endometriosis, gift from Emory University) were cultured in T75 flasks in complete media (DMEM, 10% FCS, 1% P/S). Cells were treated with 1% PF (control and endo patients) in charcoal stripped media containing 0.1% FCS, for 48 hours. A subset of cells were also treated with GSK126 or EPZ-6438 (FIG. 15), at various concentrations for 24 hours. Cells were collected post-treatment for RNA (PCR) and protein analysis (Western blotting).

Western Blotting. PF treated endometrial cells that were collected for protein were ran on the automated western blotting system WES (Protein Simple) using EZH2, and H3K27me3 (Cell Signaling) and the HRP-conjugated rabbit secondary antibody (Protein Simple). Plate 250 kDa-12 kDA/25 Capillary) were run at the default setting and results were analyzed using the Compass for Wes software.

xCELLigence. EOOF5 cells (primary endometrial cells) was plated at 10,000 cells per well using xCELLigence technology. Plates that have gold electrodes attached to the bottom were utilized. The electrodes produce electrons, which interact with the solution, completing a circuit. As the number of adhered cells in the plate increases, the more this interferes with circuit completion. Cells were treated with either 1% control or endo PF alone or treated with PF for 24 hours before being treated with either 1 µM GSK, 2.5 µM GSK, or 2.5 µM EPZ. Cells were also treated with drug alone. % Cell Impedance (CI) was calculated compared to CF media.

Statistics. Statistical analysis was performed using GraphPad Prism 8.

Example 8—Bidirectional Effects of EZH2 Inhibitor in Endometriosis

Based on the foregoing studies, it was appreciated that the polycomb-group (PcG) of proteins work as part of an epigenetic network and play a role in the development and/or progression of endometriosis. Experiments were thus undertaken to determine whether the components of peritoneal fluid (PF) played a dynamic role in the epigenetic pathway in endometriosis and whether an inhibitor of the PRC2 complex would reduce or prevent any changes mediated by PF.

Figure 16A:
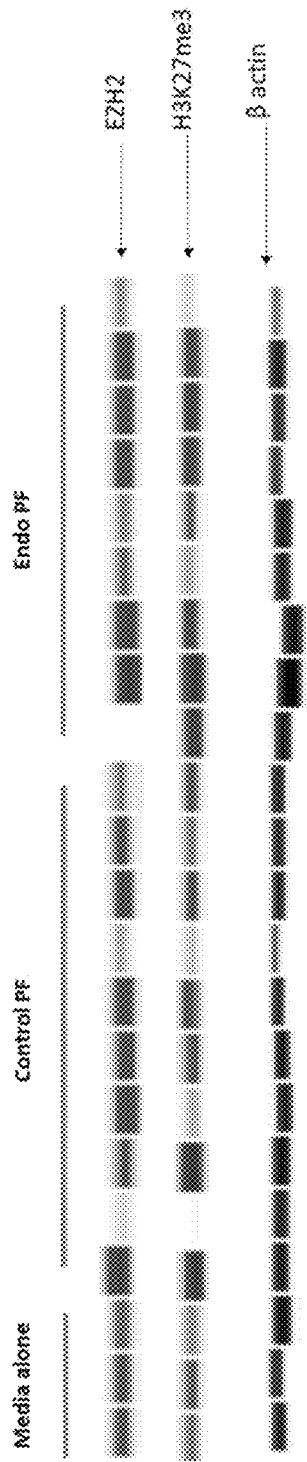
FIGS. 16A-16B show Western blots for EZH2, and H3K27me3 in PF-treated cells (FIG. 16A), and densitometric analysis of the Western blots, where relative protein expression of EZH2 and H3K27me3 in PF-treated cells was calculated in relation to a media control (FIG. 16B).
Figure 16B:
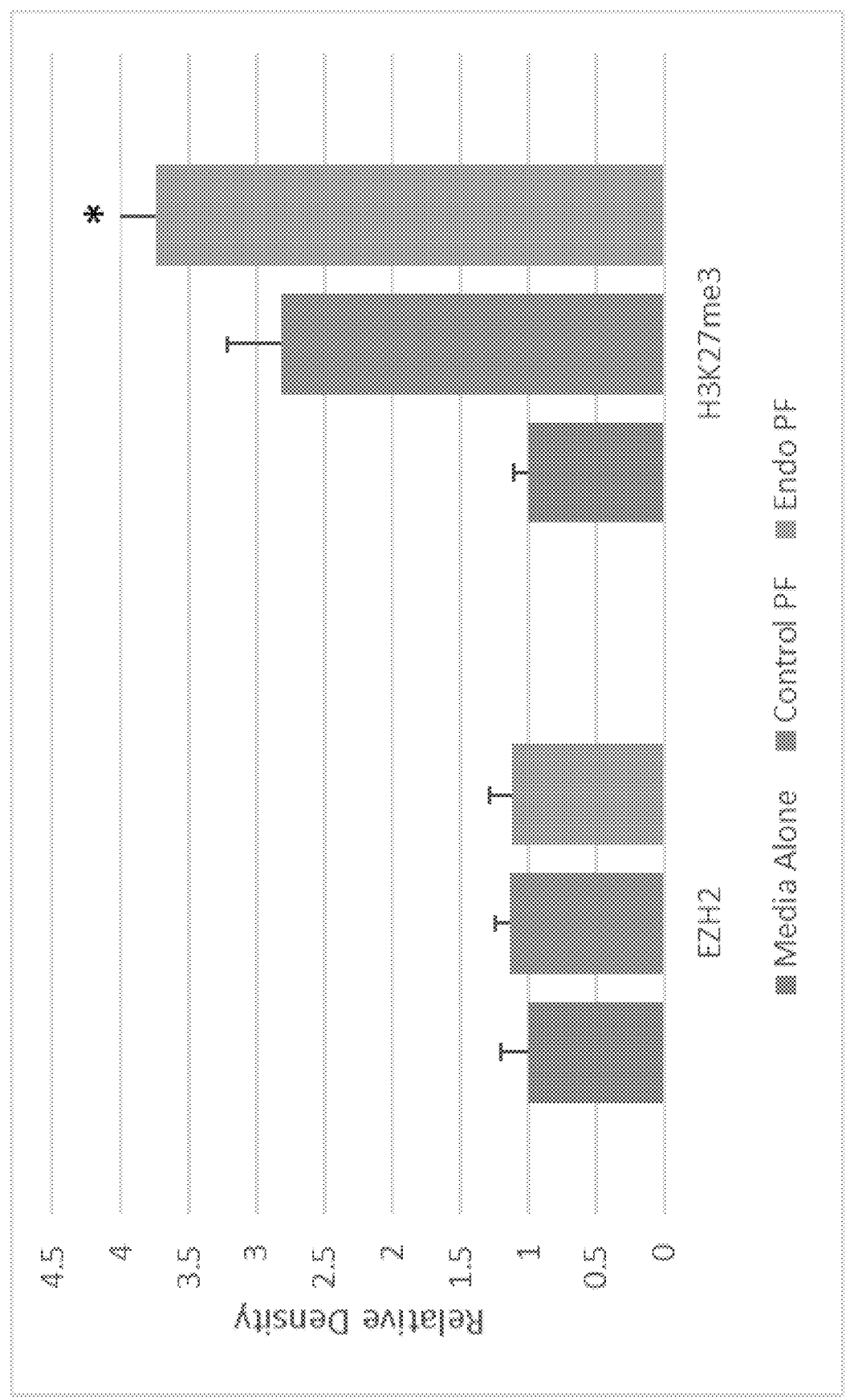
Figure 17:
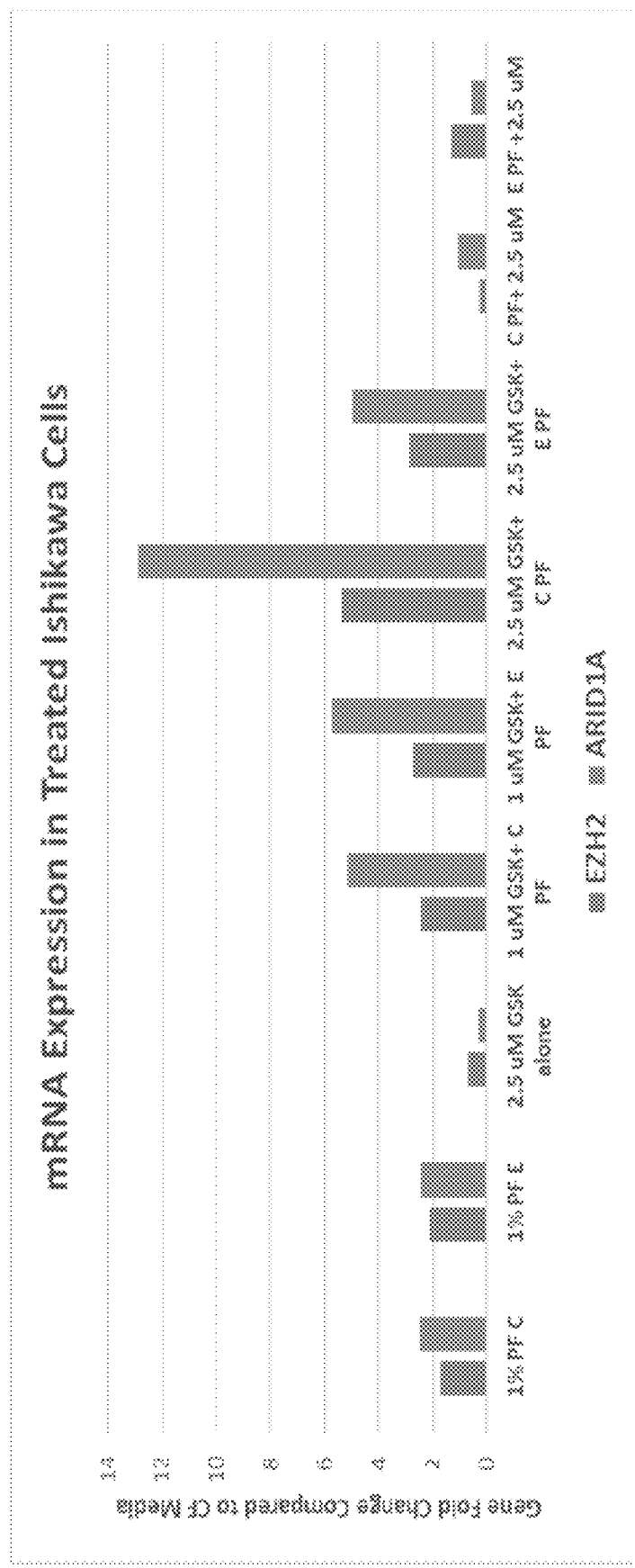
FIG. 17 includes graphs showing mRNA analysis on Ishikawa Cells treated with PF and/or GSK 126.
Figure 18:
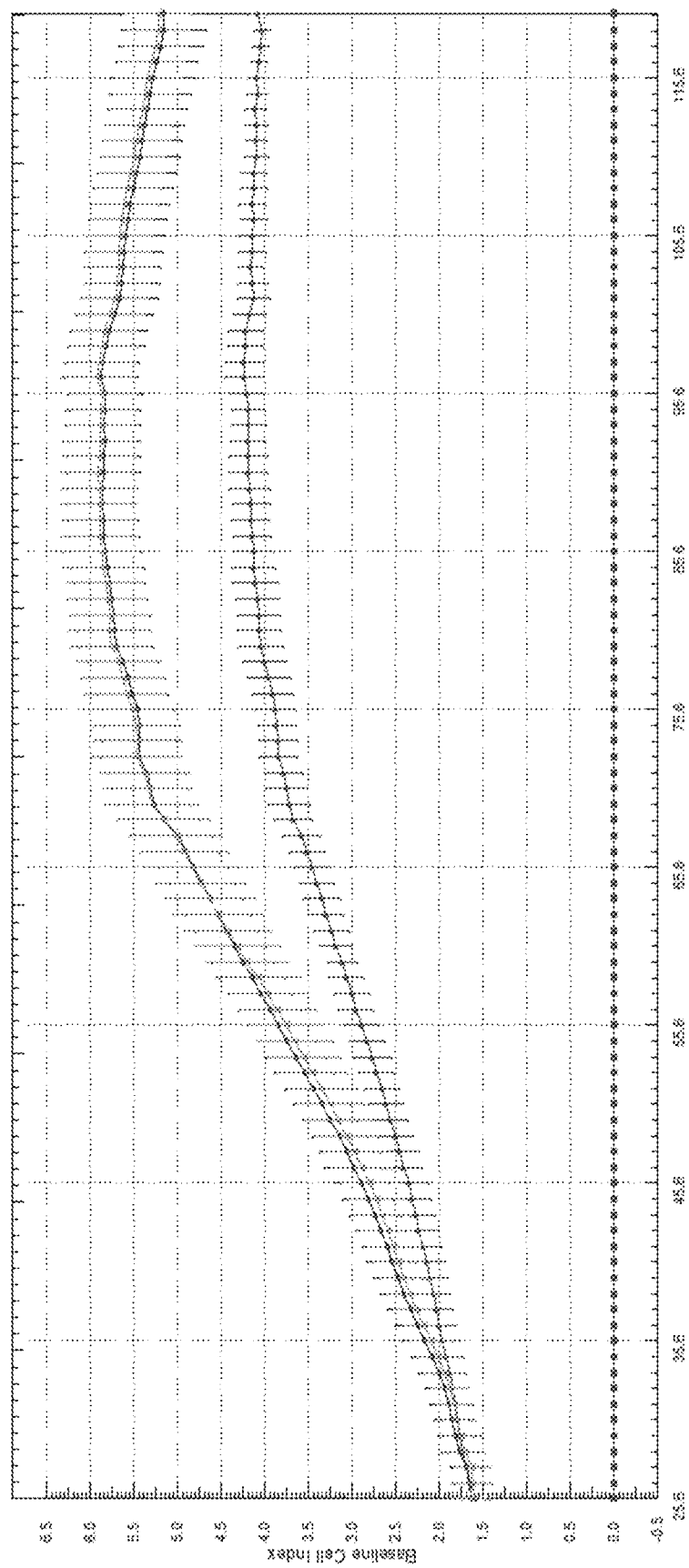
FIG. 18 includes Cell Index (CI) plots showing plots of media alone (red, n=3), 1% control PF alone (n=7, in triplicates, blue), 1% endo PF alone (n=7, in triplicates, green), and wells with no cells (brown) taken from the xCELLigence analysis. Average cell indexes (CI) of all wells, along with their standard deviation, are plotted. PFs were added at 24 hours after plating and left in the xCELLigence machine for 120 hours.
Figure 19A:
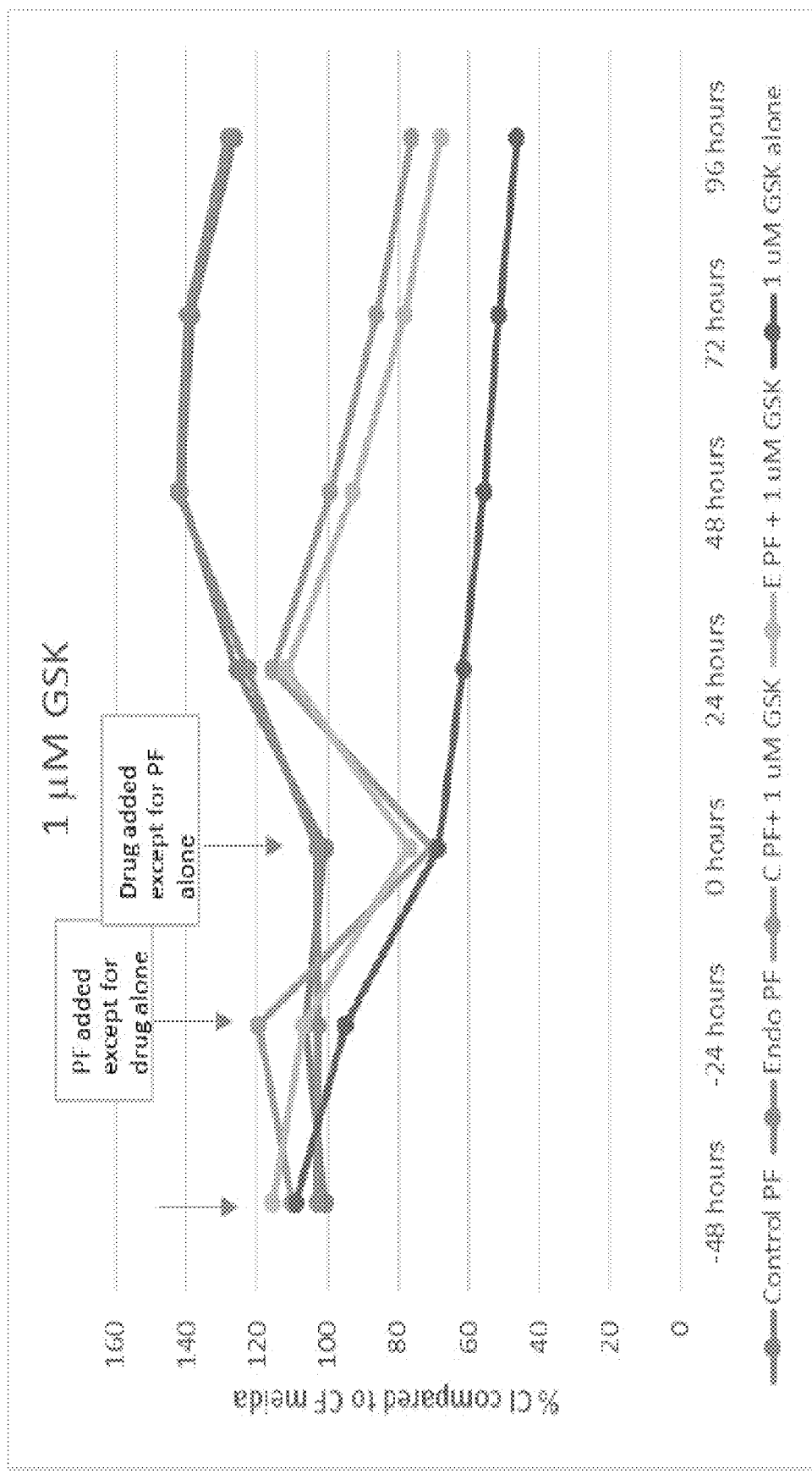
FIGS. 19A-19E show plots of % CI at various time points for E00F5 cells treated with PF and/or GSK 126 or EPZ-6438 as indicated.
Figure 19B:
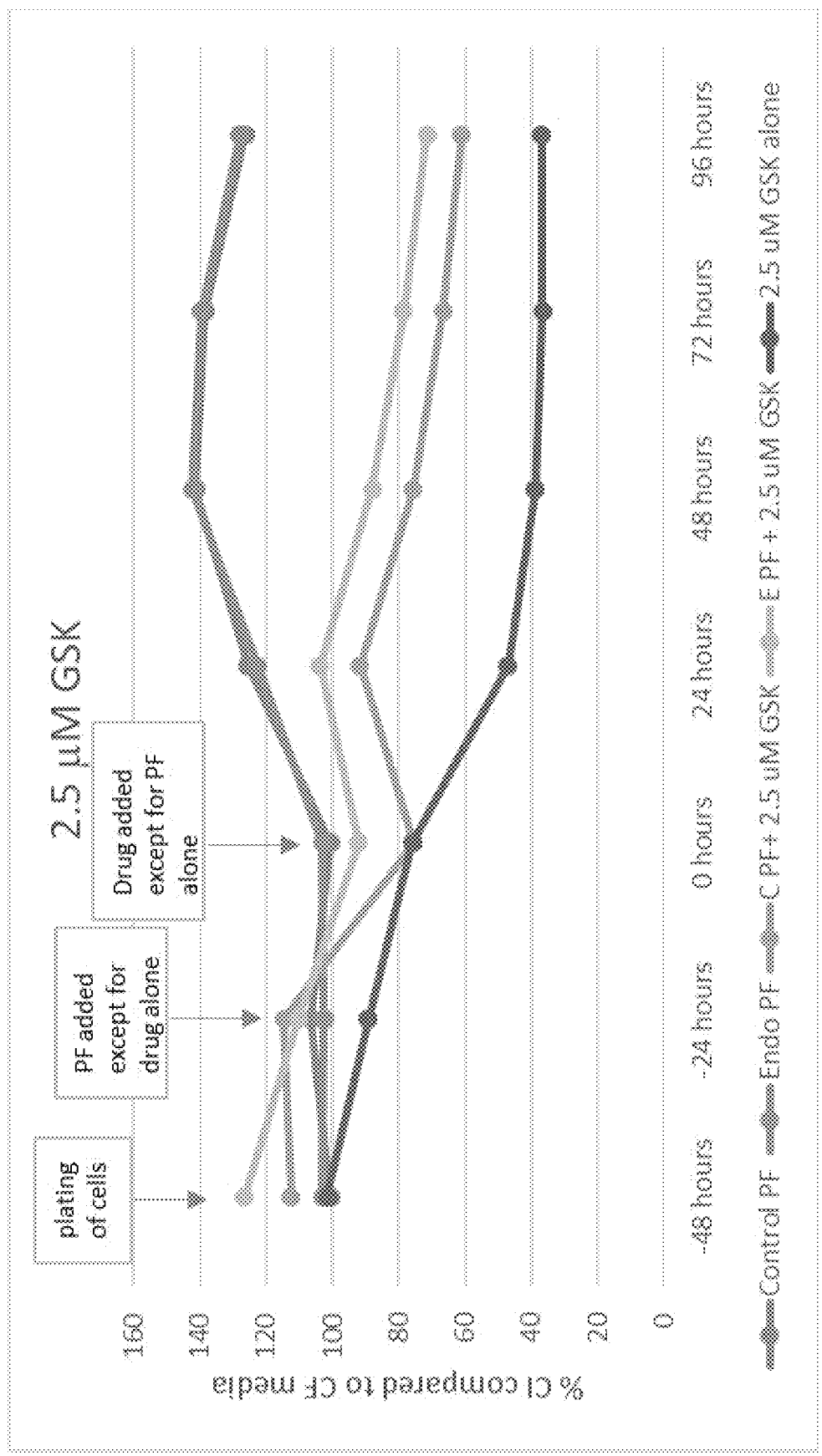
Figure 19C:
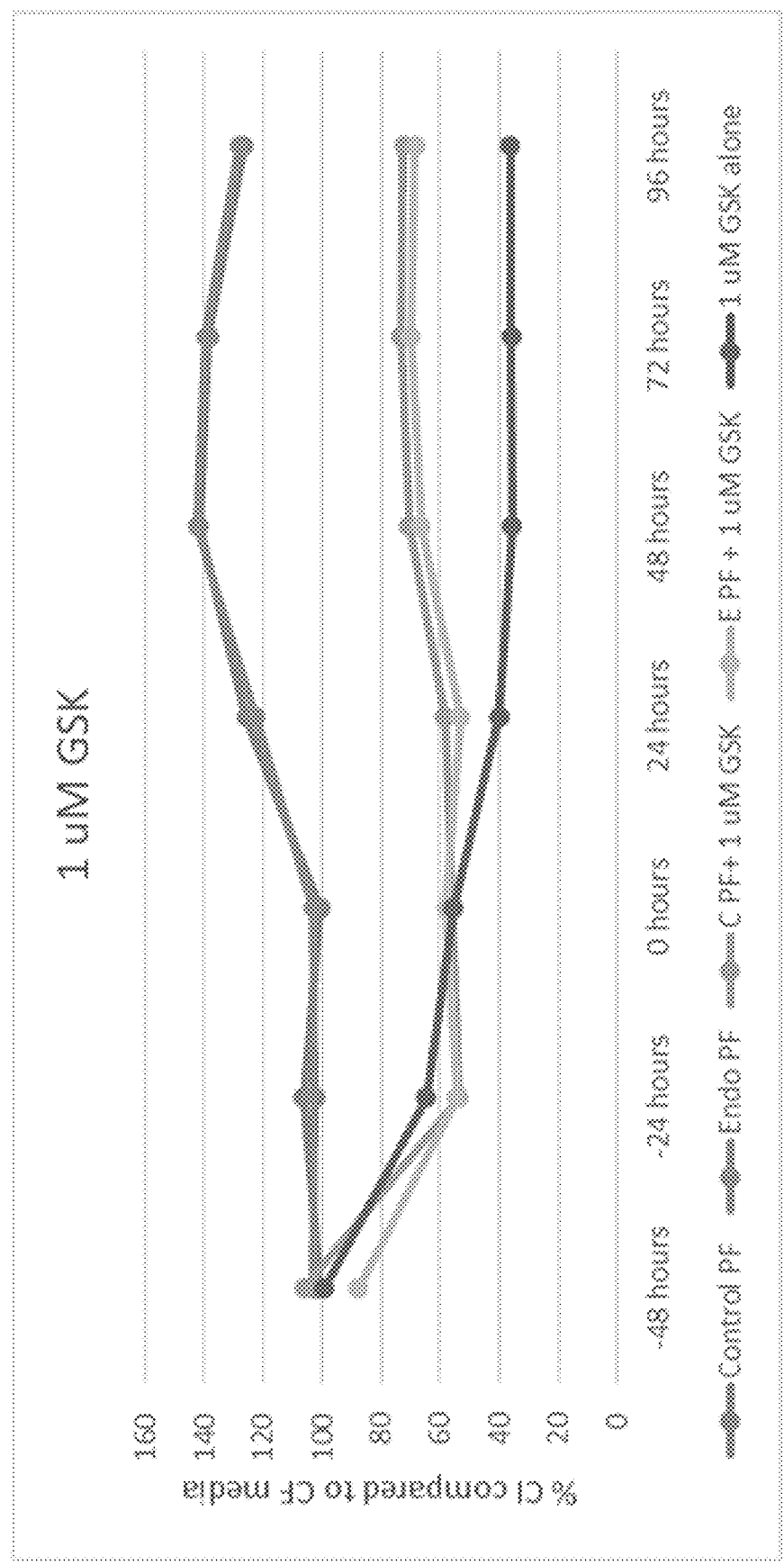
Figure 19D:
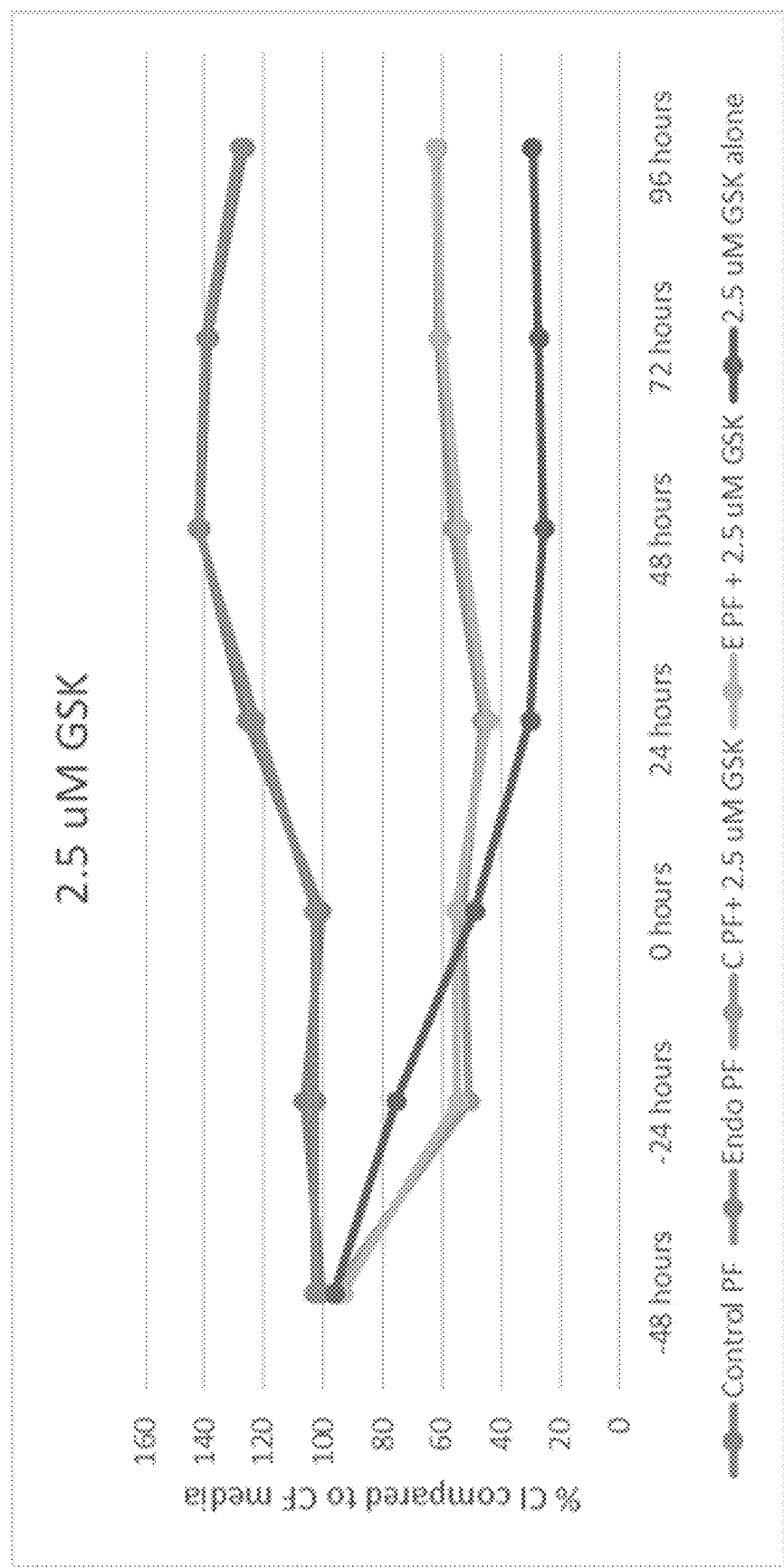
Figure 19E:
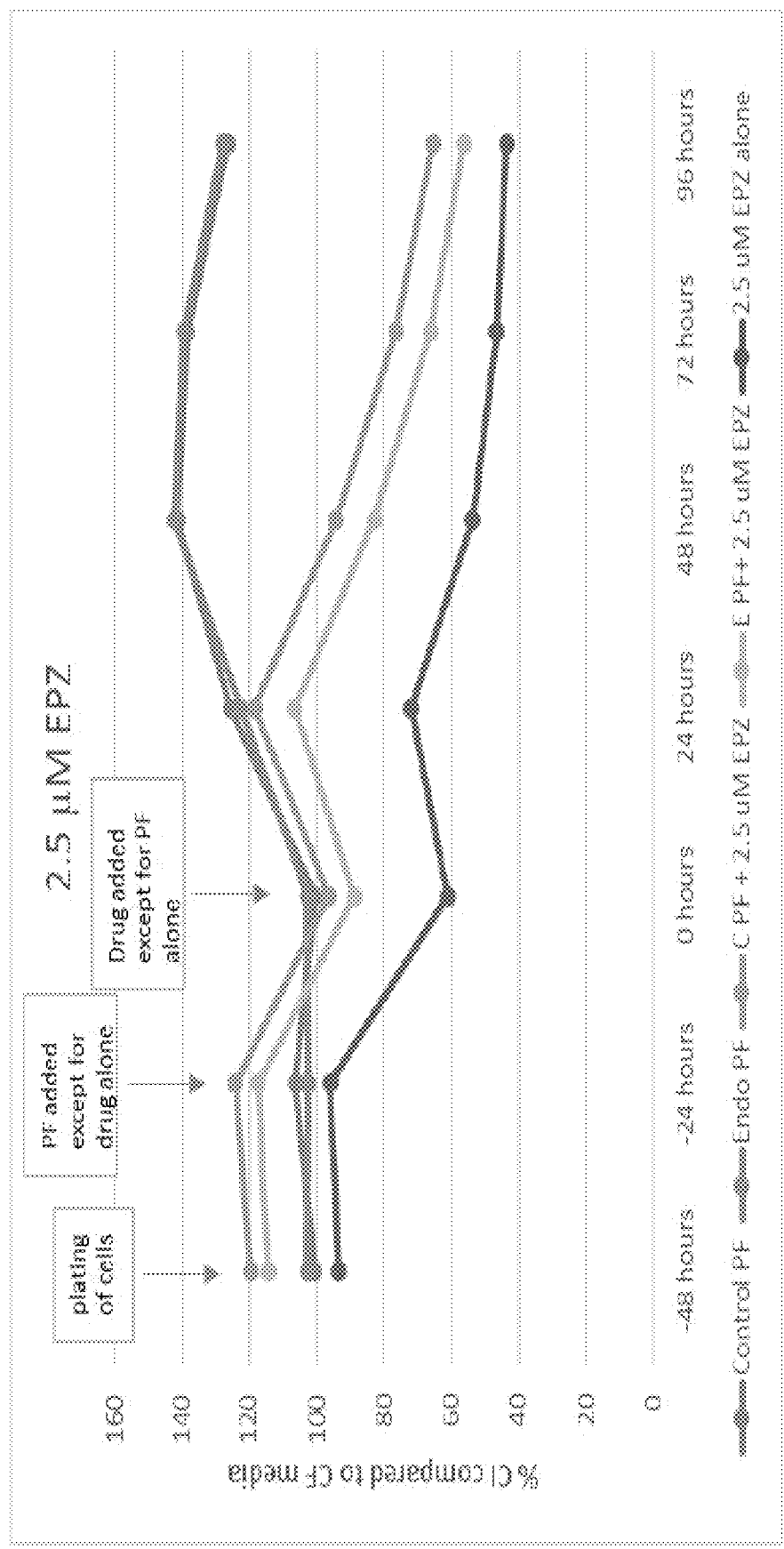

As shown in FIGS. 16A-16B, Western blots for EZH2, and H3K27me3 in PF-treated cells and subsequent densitometric analysis of those Western blots revealed that 3K27me3 levels were 3.74-fold higher in endo PF treated cells than in media control ($p<0.05$. EZH2 was normalized using β-actin and H3K27me3 was normalized using H3). Additionally, as shown in FIG. 17, mRNA analysis on Ishikawa Cells treated with PF and/or GSK 126 showed a bidirectional effect of GSK 126 on EZH2 expression depending on the order of the drug treatment in comparison to the treatment of control or endo PF alone. Similar trends were seen in ARID1A. The differences in expression levels between ARID1A and EZH2 could be explained by the antagonistic relationship between the two genes. Additionally, as depicted in FIGS. 18 and 19A-19E, plots of percentages of cell indexes (CI) at various time points for EOOF5 cells treated with PF and/or GSK 126 or EPZ-6438 showed that cells treated with PF and drug had a decrease in cell growth compared to PF alone. No significant differences was seen between the effects of GSK126 and EPZ-6438. In the plots of % CI at various time points for E00F5 cells treated with 1% PF first for 24 hours followed by the drug (GSK) for 48 hours, the cells treated with PF and GSK had a decrease in cell growth (as seen by decreased CI) compared to PF alone but not at same levels as drug alone indicating that the PF may be playing a role in inhibiting the drug from working initially. In total, however, the results in FIGS. 19A-19B shows that an EZH2 inhibitor (GSK 126) added after the PF pretreatment was able to lower the cell growth induced by PF. Moreover, in plots of % CI at various time points for EOOF5 cells treated with GSK first (for 24 hours) followed by the 1% PF treatment for another 48 hours (FIGS. 19C-19D), a significant decrease in % CI was seen when treated with drug first but a slow increase is seen after PF is adding suggesting that PF is having an effect in the cells. In this regard, in contrast to the previous experiment, when the drug (GSK 126) was added first followed by the PF, the drug was more effective in lowering cell growth due to PF treatment.

The results from the human endometrial cells treated with 1% PF showed that endometriotic PF does cause increases in PRC2 complex proteins which was believed to be leading to the observed increased proliferation. GSK 126 and EPZ-6438 treatment showed a concentration dependent decrease in cell viability and growth in the presence of PF. mRNA results suggest for an intermediate pathway that is being modulated by the PF. Inhibition of EZH2 by GSK 126 could be causing an increased expression of other proteins in the network.

Example 9—Epigenetic Crosstalk in PF-Treated Cells

Chromatin Immunoprecipitation was also used to analyze the interactions between JARID2 and EZH2 and genes associated with the polycomb and trithorax complexes, normalized to IgG. Table 3 below shows fold change values that represent the ratio of enrichment/binding of JARID2 or EZH2 to various genes in endo PF-treated cells (n=3) to enrichment in control PF-treated cells (n=3), where genes with a p-value<0.05 are shown and the p-value is shown as bold and italicized. EZH1 and EZH2 are also shown but did not have a significant p-value for either JARID2 or EZH2 when comparing the two cell treatments. Table 4 shows fold change values representing the ratio of enrichment/binding in EZH2 precipitated cells (n=3) to enrichment in JARID2 precipitated cells (n=3) for both cell treatments, where p-values<0.05 are shown as bold and italicized along with EZH1, EZH2, and JARID2, which did not show significant p-values for either treatment. In total, the additional chromatin immunoprecipitation experiment showed that EZH2 and JARID2 co-exist, since pulling down EZH2 also pulled down JARID2; however, the reverse was not seen, i.e. when JARID2 was pulled down, there was no concomitant increase in EZH2.

TABLE 3

| A | | Jarid 2 | | EZH2 | |
|---|---|---|---|---|---|
| Symbol | Gene Name | Fold Change (endo PF/ control PF) | p-value | Fold Change (endo PF/ control PF) | p-value |
| ARID1A | AT rich interactive domain 1A (SWI-like) | 3.39 | 0.0117 | 10.65 | 0.1342 |
| ASXL2 | Additional sex combs like 2 (*Drosophilia*) | 4.51 | 0.2999 | 8.88 | 0.0395 |
| CXXC1 | CXXC finger protein 1 | 3.70 | 0.0139 | 8.56 | 0.1014 |
| DNMT3B | DNA (cytosine-5-)-methyltransferase 3 beta | 1.13 | 0.8213 | 4.25 | 0.0165 |
| EZH1 | Enhancer of zeste homolog 1 (*Drosophilia*) | 1.4713 | 0.7986 | 12.11 | 0.259 |
| EZH2 | Enhancer of zeste homolog 2 (*Drosophilia*) | 0.3789 | 0.5621 | 12.79 | 0.2746 |
| INO80 | INO80 homolog (*S. cerevisiae*) | 1.50 | 0.6214 | 3.76 | 0.0182 |
| JARID 2 | Jumonji. AT rich interactive domain 2 | 2.92 | 0.2653 | 5.05 | 0.0498 |
| PHF1 | PHD finger protein 1 | 4.55 | 0.0316 | 13.31 | 0.1494 |

TABLE 4

| B | | Control PF | | Endo PF | |
|---|---|---|---|---|---|
| Symbol | Gene Name | Fold Change (Jarid2/ EZH2) | p-value | Fold Change (Jarid2/ EZH2) | p-value |
| DNMT3B | DNA Cytosine-5-)-methyltransferase 3 beta | 2.49 | 0.0164 | 0.66 | 0.385 |
| E2F6 | E2F Transcription Factor | 4.52 | 0.00027 | 0.51 | 0.4839 |
| EZH1 | Enhancer of zeste homolog 1 (*Drosophilia*) | 0.91 | 0.9143 | 0.34 | 0.3762 |
| EZH2 | Enhancer of zeste homolog 2 (*Drosophilia*) | 3.59 | 0.3551 | 0.68 | 0.6713 |
| JARID 2 | Jumonji. AT rich interactive domain 2 | 1.6 | 0.6838 | 0.92 | 0.8731 |
| MTF2 | Metal response element binding transcription factor 2 | 15.63 | 0.0234 | 0.67 | 0.6671 |
| SMARCA5 | SWI/SNF related, matrix associated, actin dependent regulator of chromatin, subfamily a, member 5 | 8.13 | 0.039 | 0.73 | 0.7004 |

All publications, patents, and patent applications mentioned in this specification are herein incorporated by reference to the same extent as if each individual publication, patent, or patent application was specifically and individually indicated to be incorporated by reference.

It will be understood that various details of the presently-disclosed subject matter can be changed without departing from the scope of the subject matter disclosed herein. Furthermore, the foregoing description is for the purpose of illustration only, and not for the purpose of limitation.

REFERENCES

Arosh, J. A., Lee, J., Balasubbramanian, D., Stanley, J. A., Long, C. R., Meagher, M. W., . . . Banu, S. K. (2015). Molecular and preclinical basis to inhibit PGE2 receptors EP2 and EP4 as a novel nonsteroidal therapy for endometriosis. *Proc Natl Acad Sci USA*, 112(31), 9716-9721. doi: 10.1073/pnas.1507931112

Bamidele, A. O., Svingen, P. A., Sagstetter, M. R., Sarmento, O. F., . . . Faubion Jr., W. A. (2019). Disruption of FOXP3-EZH2 Interaction Represents a Pathobiological Mechanism in Intestinal Inflammation. *Cellular and Molecular Gastroenterology and Hepatology*, 7(1), 55-71. doi: 10.1016/j.cmgh.2018.08.009

Basta, P., Majka, M., Jozwicki, W., Lukaszewska, E., Knafel, A., Grabiec, M., . . . Wicherek, L. (2010). The frequency of CD25+CD4+ and FOXP3+ regulatory T cells in ectopic endometrium and ectopic decidua. *Reprod Biol Endocrinol*, 8, 116. doi: 10.1186/1477-7827-8-116

Berbic, M., & Fraser, I. S. (2011). Regulatory T cells and other leukocytes in the pathogenesis of endometriosis. *J Reprod Immunol*, 88(2), 149-155. doi: 10.1016/j.jri.2010.11.004

Berbic, M., Hey-Cunningham, A. J., Ng, C., Tokushige, N., Ganewatta, S., Markham, R., . . . Fraser, I. S. (2010). The role of Foxp3+ regulatory T-cells in endometriosis: a potential controlling mechanism for a complex, chronic immunological condition. *Hum Reprod,* 25(4), 900-907. doi: 10.1093/humrep/deq020

Bird, A. (2007). Perceptions of epigenetics. *Nature,* 447 (7143), 396-398. doi: 10.1038/nature05913

Brien, G. L., Gambero, G., O'Connell, D. J., Jerman, E., Turner, S. A., Egan, C. M., . . . Bracken, A. P. (2012). Polycomb PHF19 binds H3K36me3 and recruits PRC2 and demethylase NO66 to embryonic stem cell genes during differentiation. *Nat Struct Mol Biol,* 19(12), 1273-1281. doi: 10.1038/nsmb.2449

Bulun, S. E., Cheng, Y. H., Yin, P., Imir, G., Utsunomiya, H., Attar, E., . . . Julie Kim, J. (2006). Progesterone resistance in endometriosis: link to failure to metabolize estradiol. *Mol Cell Endocrinol,* 248(1-2), 94-103. doi: 10.1016/j.mce.2005.11.041

Burney, R. O., & Giudice, L. C. (2012). Pathogenesis and pathophysiology of endometriosis. *Fertil Steril,* 98(3), 511-519. doi: 10.1016/j.fertnstert.2012.06.029

Cao, R., Wang, L., Wang, H., Xia, L., Erdjument-Bromage, H., Tempst, P., . . . Zhang, Y. (2002). Role of histone H3 lysine 27 methylation in Polycomb-group silencing. *Science,* 298(5595), 1039-1043. doi: 10.1126/science.1076997

Cho, S., Mutlu, L., Zhou, Y., & Taylor, H. S. (2016). Aromatase inhibitor regulates let-7 expression and let-7f-induced cell migration in endometrial cells from women with endometriosis. *Fertil Steril,* 106(3), 673-680. doi: 10.1016/j.fertnstert.2016.05.020

Ciarmela, P., Critchley, H., Christman, G. M., & Reis, F. M. (2013). Pathogenesis of endometriosis and uterine fibroids. *Obstet Gynecol Int,* 2013, 656571. doi: 10.1155/2013/656571

Colon-Caraballo, M., Monteiro, J. B., & Flores, I. (2015). H3K27me3 is an Epigenetic Mark of Relevance in Endometriosis. *Reprod Sci,* 22(9), 1134-1142. doi: 10.1177/1933719115578924

Colon-Caraballo, M., Torres-Reveron, A., Soto-Vargas, J. L., Young, S. L., Lessey, B., Mendoza, A., Urrutia, R.,& Flores, I. (2018). Effects of histone methyltransferase inhibition in endometriosis. *Biology of Reproduction,* 99(2), 293-307. doi: 10.1093/biolre/ioy030

Escobar, T. M., Kanellopoulou, C., Kugler, D. G., Kilaru, G., Nguyen, C. K., Nagarajan, V., . . . Muljo, S. A. (2014). miR-155 activates cytokine gene expression in Th17 cells by regulating the DNA-binding protein Jarid2 to relieve polycomb-mediated repression. *Immunity,* 40(6), 865-879. doi: 10.1016/j.immuni.2014.03.014

Fuks, F. (2005). DNA methylation and histone modifications: teaming up to silence genes. *Curr Opin Genet Dev,* 15(5), 490-495. doi: 10.1016/j.gde.2005.08.002

Gao, Y., Tang, J., Chen, W., Li, Q., Nie, J., Lin, F., . . . Li, B. (2015). Inflammation negatively regulates FOXP3 and regulatory T-cell function via DBC1. *Proc Natl Acad Sci USA,* 112(25), E3246-3254. doi: 10.1073/pnas.1421463112

Geisler, S. J., & Paro, R. (2015). Trithorax and Polycomb group-dependent regulation: a tale of opposing activities. *Development,* 142(17), 2876-2887. doi: 10.1242/dev.120030

Ghislin, S., Deshayes, F., Middendorp, S., Boggetto, N., & Alcaide-Loridan, C. (2012). PHF19 and Akt control the switch between proliferative and invasive states in melanoma. *Cell Cycle,* 11(8), 1634-1645. doi: 10.4161/cc.20095

Giudice, L. C. (2010). Clinical practice. Endometriosis. *N Engl J Med,* 362(25), 2389-2398. doi: 10.1056/NEJMcp1000274

Guo, S. W. (2009). Epigenetics of endometriosis. *Mol Hum Reprod,* 15(10), 587-607. doi: 10.1093/molehr/gap064

Jablonski, K. A., Gaudet, A. D., Amici, S. A., Popovich, P. G., & Guerau-de-Arellano, M. (2016). Control of the Inflammatory Macrophage Transcriptional Signature by miR-155. *PLoS One,* 11(7), e0159724. doi: 10.1371/journal.pone.0159724

Klose, R. J., Kallin, E. M., & Zhang, Y. (2006). JmjC-domain-containing proteins and histone demethylation. *Nat Rev Genet,* 7(9), 715-727. doi: 10.1038/nrg1945

Kohlhaas, S., Garden, O. A., Scudamore, C., Turner, M., Okkenhaug, K., & Vigorito, E. (2009). Cutting edge: the Foxp3 target miR-155 contributes to the development of regulatory T cells. *J Immunol,* 182(5), 2578-2582. doi: 10.4049/jimmunol.0803162

Kondo, Y. (2009). Epigenetic cross-talk between DNA methylation and histone modifications in human cancers. *Yonsei Med J,* 50(4), 455-463. doi: 10.3349/ymj.2009.50.4.455

Kooistra, S. M., & Helin, K. (2012). Molecular mechanisms and potential functions of histone demethylases. *Nat Rev Mol Cell Biol,* 13(5), 297-311. doi: 10.1038/nrm3327

Kuzmichev, A., Nishioka, K., Erdjument-Bromage, H., Tempst, P., & Reinberg, D. (2002). Histone methyltransferase activity associated with a human multiprotein complex containing the Enhancer of Zeste protein. *Genes Dev,* 16(22), 2893-2905. doi: 10.1101/gad.1035902

Landeira, D., & Fisher, A. G. (2011). Inactive yet indispensable: the tale of Jarid2. *Trends Cell Biol,* 21(2), 74-80. doi: 10.1016/j.tcb.2010.10.004

Li, G., Margueron, R., Ku, M., Chambon, P., Bernstein, B. E., & Reinberg, D. (2010). Jarid2 and PRC2, partners in regulating gene expression. *Genes Dev,* 24(4), 368-380. doi: 10.1101/gad.1886410

Lowry, O. H., Rosebrough, N. J., Farr, A. L., & Randall, R. J. (1951). Protein measurement with the Folin phenol reagent. *J Biol Chem,* 193(1), 265-275.

Mochizuki-Kashio, M., Aoyama, K., Sashida, G., Oshima, M., Tomioka, T., Muto, T., . . . Iwama, A. (2015). Ezh2 loss in hematopoietic stem cells predisposes mice to develop heterogeneous malignancies in an Ezh1-dependent manner. *Blood,* 126(10), 1172-1183. doi: 10.1182/blood-2015-03-634428

Nasu, K., Kawano, Y., Tsukamoto, Y., Takano, M., Takai, N., Li, H., . . . Narahara, H. (2011). Aberrant DNA methylation status of endometriosis: epigenetics as the pathogenesis, biomarker and therapeutic target. *J Obstet Gynaecol Res,* 37(7), 683-695. doi: 10.1111/j.1447-0756.2011.01663.x Nishida, M., Kasahara, K., Kaneko, M., Iwasaki, H., & Hayashi, K. (1985). [Establishment of a new human endometrial adenocarcinoma cell line, Ishikawa cells, containing estrogen and progesterone receptors]. *Nihon Sanka Fujinka Gakkai Zasshi,* 37(7), 1103-1111.

Olkowska-Truchanowicz, J., Bocian, K., Maksym, R. B., Bialoszewska, A., Wlodarczyk, D., Baranowski, W., . . . Malejczyk, J. (2013). CD4(+) CD25(+) FOXP3(+) regulatory T cells in peripheral blood and peritoneal fluid of patients with endometriosis. *Hum Reprod,* 28(1), 119-124. doi: 10.1093/humrep/des346

Palma, C. A., Al Sheikha, D., Lim, T. K., Bryant, A., Vu, T. T., Jayaswal, V., & Ma, D. D. (2014). MicroRNA-155 as an inducer of apoptosis and cell differentiation in Acute Myeloid Leukaemia. *Mol Cancer,* 13, 79. doi: 10.1186/1476-4598-13-79

Pasini, D., Cloos, P. A., Walfridsson, J., Olsson, L., Bukowski, J. P., Johansen, J. V., . . . Helin, K. (2010).

JARID2 regulates binding of the Polycomb repressive complex 2 to target genes in ES cells. *Nature,* 464(7286), 306-310. doi: 10.1038/nature08788

Platteeuw, L., & D'Hooghe, T. (2014). Novel agents for the medical treatment of endometriosis. *Curr Opin Obstet Gynecol,* 26(4), 243-252. doi: 10.1097/GCO.0000000000000084

Podgaec, S., Rizzo, L. V., Fernandes, L. F., Baracat, E. C., & Abrao, M. S. (2012). CD4(+) CD25(high) Foxp3(+) cells increased in the peritoneal fluid of patients with endometriosis. *Am J Reprod Immunol,* 68(4), 301-308. doi: 10.1111/j.1600-0897.2012.01173.x Qin, S., Guo, Y., Xu, C., Bian, C., Fu, M., Gong, S., & Min, J. (2013). Tudor domains of the PRC2 components PHF1 and PHF19 selectively bind to histone H3K36me3. *Biochem Biophys Res Commun,* 430(2), 547-553. doi: 10.1016/j.bbrc.2012.11.116

Ray, K., Fahrmann, J., Mitchell, B., Paul, D., King, H., Crain, C., . . . Santanam, N. (2015). Oxidation-sensitive nociception involved in endometriosis-associated pain. *Pain,* 156(3), 528-539. doi: 10.1097/01.j.pain.0000460321.72396.88

Ray, K. L., Mitchell, B. L., & Santanam, N. (2014). Power over pain: a brief review of current and novel interventions for endometriosis-associated pain. *Journal of Endometriosis and Pelvic Pain Disorders,* 6(4), 163-173. doi: 10.5301/je.5000199

Rong, R., Ramachandran, S., Santanam, N., Murphy, A. A., & Parthasarathy, S. (2002). Induction of monocyte chemotactic protein-1 in peritoneal mesothelial and endometrial cells by oxidized low-density lipoprotein and peritoneal fluid from women with endometriosis. *Fertil Steril,* 78(4), 843-848

Santanam, N., Kavtaradze, N., Murphy, A., Dominguez, C., & Parthasarathy, S. (2013). Antioxidant supplementation reduces endometriosis-related pelvic pain in humans. *Transl Res,* 161(3), 189-195. doi: 10.1016/j.trsl.2012.05.001

Shen, X., Liu, Y., Hsu, Y. J., Fujiwara, Y., Kim, J., Mao, X., . . . Orkin, S. H. (2008). EZH1 mediates methylation on histone H3 lysine 27 and complements EZH2 in maintaining stem cell identity and executing pluripotency. *Mol Cell,* 32(4), 491-502. doi: 10.1016/j.molcel.2008.10.016

Shen, Z., Chen, L., Yang, X., Zhao, Y., Pier, E., Zhang, X., . . . Xiong, Y. (2013). Downregulation of Ezh2 methyltransferase by FOXP3: new insight of FOXP3 into chromatin remodeling? *Biochim Biophys Acta,* 1833(10), 2190-2200. doi: 10.1016/j.bbamcr.2013.05.014

Son, J., Shen, S. S., Margueron, R., & Reinberg, D. (2013). Nucleosome-binding activities within JARID2 and EZH1 regulate the function of PRC2 on chromatin. *Genes Dev,* 27(24), 2663-2677. doi: 10.1101/gad.225888.113

Steffen, P. A., & Ringrose, L. (2014). What are memories made of? How Polycomb and Trithorax proteins mediate epigenetic memory. *Nat Rev Mol Cell Biol,* 15(5), 340-356. doi: 10.1038/nrm3789

Stephens, L., Whitehouse, J., & Polley, M. (2013). Western herbal medicine, epigenetics, and endometriosis. *J Altern Complement Med,* 19(11), 853-859. doi: 10.1089/acm.2012.0623

Tanaka, Y., Mori, T., Ito, F., Koshiba, A., . . . Kitawaki, J. (2017) Exacerbation of Endometriosis Due to Regulatory T-Cell Dysfunction. *The Journal of Clinical Endocrinology & Metabolism,* 102(9), 3206-3217. doi: 10.1210/jc.2017-00052

Vire, E., Brenner, C., Deplus, R., Blanchon, L., Fraga, M., Didelot, C., . . . Fuks, F. (2006). The Polycomb group protein EZH2 directly controls DNA methylation. *Nature,* 439(7078), 871-874. doi: 10.1038/nature04431

Wright, K., Mitchell, B., Santanam, N. (2017). Redox regulation of microRNAs in endometriosis-associated pain. *Redox Biology,* 12, 956-966. doi: https://doi.org/10.1016/j.redox.2017.04.037

Xiong, Y., Khanna, S., Grzenda, A. L., Sarmento, O. F., Svingen, P. A., Lomberk, G. A., . . . Faubion, W. A., Jr. (2012). Polycomb antagonizes p300/CREB-binding protein-associated factor to silence FOXP3 in a Kruppel-like factor-dependent manner. *J Biol Chem,* 287(41), 34372-34385. doi: 10.1074/jbc.M111.325332

Yao, Y., Li, G., Wu, J., Zhang, X., & Wang, J. (2015). Inflammatory response of macrophages cultured with *Helicobacter pylori* strains was regulated by miR-155. *Int J Clin Exp Pathol,* 8(5), 4545-4554.

What is claimed is:

1. A method for screening for a compound useful for treating endometriosis, comprising:
   contacting an endometrial cell with an effective amount of a test compound;
   detecting an activity level of JARID2 and miR-155 in the endometrial cell in the presence of the test compound; and
   comparing the activity level of JARID2 and miR-155 in the presence of the test compound to a control activity level of JARID2 and miR-155 in a non-contacted endometrial cell, wherein the test compound is identified as a compound useful for the treatment of endometriosis if there is a measurable decrease in the activity level of JARID2 and an increase in the activity level of miR-155 in the contacted endometrial cell as compared to the control activity level of JARID2 and miR-155.

2. The method of claim 1, further comprising determining an activity level of EZH2 and/or H3k27me3 in the contacted endometrial cell in the presence of the test compound.

3. The method of claim 1, wherein the contacted endometrial cell is obtained from a subject.

4. The method of claim 3, wherein the subject is human.

5. The method of claim 3, wherein the subject has endometriosis.

6. The method of claim 5, wherein the endometriosis is eutopic endometriosis or ectopic endometriosis.

7. The method of claim 5, wherein the subject has pain associated with the endometriosis.

\* \* \* \* \*